United States Patent [19]

Moon

[11] Patent Number: 5,090,993
[45] Date of Patent: Feb. 25, 1992

[54] FLUOROALKOXY AMINO TRIAZINES FOR CONTROL OF WEEDS IN SUGAR BEETS

[75] Inventor: Marcus P. Moon, Wilmington, Del.

[73] Assignee: E.I. Du Pont de Nemours & Company, Wilmington, Del.

[21] Appl. No.: 576,445

[22] PCT Filed: Mar. 16, 1989

[86] PCT No.: PCT/US89/00996

§ 371 Date: Sep. 14, 1990

§ 102(e) Date: Sep. 14, 1990

Related U.S. Application Data

[63] Continuation-in-part of Ser. No. 172,593, Mar. 24, 1988, abandoned.

[51] Int. Cl.$^5$ .................. C07D 251/52; A01N 43/70

[52] U.S. Cl. .......................................... 71/93; 544/208

[58] Field of Search ............................ 544/208; 71/93

[56] References Cited

FOREIGN PATENT DOCUMENTS 164269 12/1985 European Pat. Off. .
84/2245 9/1984 South Africa .

Primary Examiner—John M. Ford
Attorney, Agent, or Firm—John A. Parrish

[57] ABSTRACT

This invention comprises novel fluoroalkoxy amino triazines, agriculturally suitable compositions containing them, and their method-of-use as preemergence and/or postemergence herbicides or plant growth regulants.

23 Claims, No Drawings

FLUOROALKOXY AMINO TRIAZINES FOR CONTROL OF WEEDS IN SUGAR BEETS

RELATED APPLICATION

This application is a continuation-in-part of my co-pending application U.S. Pat. application Ser. No. 07/172,593, filed Mar. 24, 1988, now abandoned.

BACKGROUND OF THE INVENTION

U.S. Pat. No. 4,744,816, issued May 17, 1988, and EP-A-164,269, published on Dec. 11, 1985, disclose herbicidal sulfonylureas of the formula

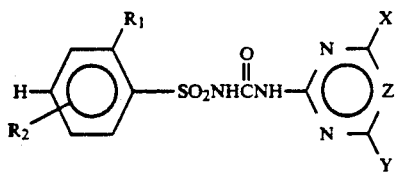

wherein
- $R_1$ is, inter alia, $CO_2R_{10}$, etc.;
- $R_2$ is H, F, Cl, Br, $CF_3$, $CH_3$, $C_2H_5$, $OCH_3$, $OC_2H_5$, $SCH_3$ or $SC_2H_5$;
- $R_{10}$ is $C_1$-$C_4$ alkyl, $CH_2CH_2OCH_3$, $CH_2CH_2Cl$, $CH_2CH=CH_2$ or $CH_2C\equiv CH$;
- $R_{14}$ is H or $C_1$-$C_2$ alkyl;
- $R_{15}$ is $C_1$-$C_2$ alkyl, $OCH_3$, $OC_2H_5$ or $CH_2CN$;
- X is $NR_{14}R_{15}$;
- Y is $OCH_2CH_2F$, $OCH_2CHF_2$ or $OCH_2CF_3$; and
- Z is CH or N.

South African Application No. 84/2245, published Sep. 28, 1984, discloses herbicidal sulfonylureas of the formula

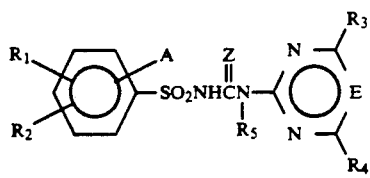

wherein
- A is $C_1$-$C_6$ haloalkyl
- Z is O or S;
- E is CH or N;
- $R_1$ is, inter alia. H, $COR_6$, etc.;
- $R_2$ is, inter alia, H, etc.;
- $R_3$ and $R_4$ are independently H, halogen, $C_1$-$C_4$ alkyl, $C_2$-$C_4$ haloalkoxy, $NR_{12}R_{13}$, etc.;
- $R_6$ is, inter alia, $C_1$-$C_4$ alkoxy, $C_1$-$C_4$ haloalkoxy, $C_2$-$C_6$ alkoxyalkoxy, etc.; and
- $R_{12}$ and $R_{13}$ are independently H or $C_1$-$C_4$ alkyl.

While these two references generically disclose some of the compounds of the instant invention, there is no specific mention of the instant compounds or their utility in sugar beets.

U.S Pat. No. 4,618,363 discloses herbicidal sulfonylureas of the formula

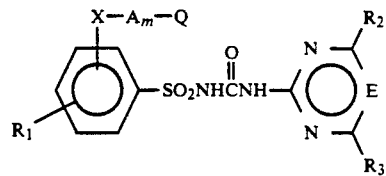

wherein
- $R_1$ is H, halogen, $NO_2$, $C_1$-$C_4$ haloalkyl, $C_1$-$C_4$ alkyl, $C_1$-$C_4$ alkoxy, $C_2$-$C_5$ alkenyl or $C_1$-$C_4$ alkoxycarbonyl;
- X is O, S, —SO— or $SO_2$;
- m is 0 or 1;
- Q is, inter alia, $R_{13}$, etc.;
- $R_{13}$ is phenyl or phenyl substituted by halogen, $NO_2$, CN, $C_1$-$C_4$ alkyl, $C_1$-$C_4$ alkoxy, $C_1$-$C_4$ alkylthio, $C_2$-$C_5$ alkenyl, $C_1$-$C_4$ haloalkyl, $C_1$-$C_4$ alkoxycarbonyl, —$NR_{45}R_{46}$, —$SO_3H$ or —$SO_2NR_{47}R_{48}$;
- $R_2$ is $C_1$-$C_3$ alkyl or $C_1$-$C_3$ alkoxy, each unsubstituted by 1 to 3 halogen atoms;
- $R_3$ is, inter alia, —$NR_4R_5$, etc.; and
- E is N or CH.

While this reference generically discloses some of the compounds of the instant invention, there is no specific mention of the instant compounds or their utility in sugar beets.

SUMMARY OF THE INVENTION

This invention comprises novel compounds of Formula I, agriculturally suitable compositions containing them, and their method-of-use as preemergence and/or postemergence herbicides or plant growth regulants.

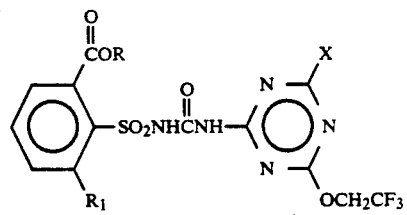

wherein
- R is $C_1$-$C_4$ alkyl, $CH_2CH=CH_2$, $CH_2C\equiv CH$, cyclopropylmethyl or $CH_2CH_2R_2$;
- $R_1$ is $C_1$-$C_2$ alkyl, $C_1$-$C_2$ haloalkyl, $CH_2CN$, $CH_2CH_3$, $C_1$-$C_3$ alkoxy, $C_1$-$C_3$ alkylthio, phenylthio or $NR_3R_4$;
- $R_2$ is $C_1$-$C_2$ alkoxy, $C_1$-$C_2$ alkylthio, CN or halogen;
- $R_3$ and $R_4$ are independently H or $CH_3$; and
- X is $NHCH_3$, $N(CH_3)_2$ or $N(CH_3)OCH_3$; provided that when $R_1$ is $OCH_2CH_3$ or $CH_2OCH_3$, then R is other than $CH_3$;

and their agriculturally suitable salts.

In the above definitions, the term "alkyl" includes straight chain or branched alkyl, e.g., methyl, ethyl, n-propyl, isopropyl or the different butyl isomers.

Alkoxy includes methoxy and ethoxy.

Alkylthio includes methylthio and ethylthio.

The term "halogen," either alone or in compound words such as "haloalkyl," means fluorine, chlorine, bromine or iodine. Further, when used in compound words such as "haloalkyl" said alkyl may be partially or fully substituted with halogen atoms, which may be the same or different. Examples of haloalkyl include $CF_3$, $CH_2CH_2F$, $CF_2CF_3$ and $CH_2CHFCl$.

The total number of carbon atoms in a substituent group is indicated by the $C_i$-$C_j$ prefix where i and j are numbers from 1 to 4. For example, $C_1$-$C_4$ alkyl would designate methyl, ethyl and the different propyl and butyl isomers; $C_1$-$C_2$ alkylthio would designate methylthio and ethylthio; $C_1$-$C_2$ alkoxy would designate methoxy and ethoxy.

Preferred for reasons of their higher herbicidal activity, greater safety to sugar beets and/or more favorable ease of synthesis are:

1. Compounds of Formula I wherein
   R is $C_1$-$C_4$ alkyl;
   $R_1$ is $C_1$-$C_2$ alkyl; and
   X is $NHCH_3$ or $N(CH_3)_2$.
2. Compounds of Formula I wherein
   R is $C_1$-$C_4$ alkyl;
   $R_1$ is $C_1$-$C_2$ haloalkyl; and
   X is $NHCH_3$ or $N(CH_3)_2$.
3. Compounds of Preferred 1 wherein
   R is $C_1$-$C_3$ alkyl; and
   X is $NHCH_3$.
4. Compounds of Preferred 1 wherein
   R is $C_1$-$C_3$ alkyl; and
   X is $N(CH_3)_2$.

Specifically preferred for reasons of highest herbicidal activity, greatest safety to sugar beets and/or most favorable ease of synthesis are:

Ethyl 2-[[[[[4-(dimethylamino)-6-(2,2,2-trifluoroethoxy)-1,3,5-triazin-2-yl]amino]carbonyl]amino]sulfonyl]-3-methylbenzoate, melting point 134–142° C.; and Methyl 2-[[[[[4-(dimethylamino)-6-(2,2,2-trifluoroethyoxy)-1,3,5-triazin-2-yl]amino]carbonyl]amino]sulfonyl]-3-methylbenzoate, melting point 150–160° C.

DETAILED DESCRIPTION OF THE INVENTION

Synthesis

The following discussion represents a general outline for the preparation of the compounds of this invention. All of the syntheses described below are multistep with one or more methods being taught for each step. This allows for a wide variety of possible synthetic pathways to prepare a particular compound of Formula I. The proper choice of the synthetic pathway and the best ordering of the reaction sequences for each individual will be known to one skilled in the art.

The compounds of Formula I can be prepared by the methods shown in Equations 1 and 2.

As shown in Equation 1, many of the compounds of Formula I can be prepared by reacting a silyl sulfonamide of Formula II with a heterocyclic carbamate of Formula III.

Equation 1:

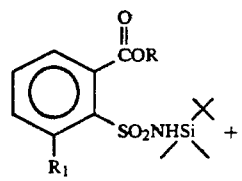

II

-continued

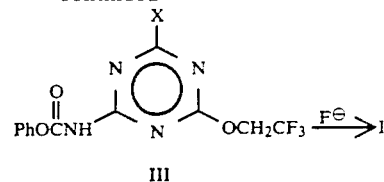

III

The reaction is carried out at 0° to 50° C. in a solvent such as acetonitrile, dioxane, or tetrahydrofuran in the presence of a fluoride ion source such as cesium fluoride or tetrabutylammonium fluoride for 0.1 to 2 hours.

Alternatively, some of the sulfonamides of Formula IV can be prepared and reacted with heterocyclic carbamates of Formula III to give compounds of Formula I as shown in Equation 2.

Equation 2:

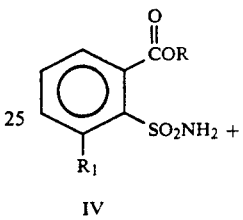

IV

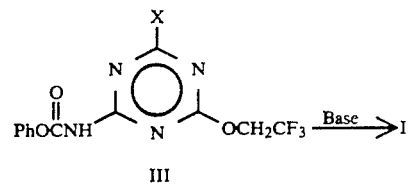

III

The reaction is carried out at 0° to 50° C. in a solvent such as acetonitrile, dioxane, or tetrahydrofuran in the presence of a non-nucleophilic base such as DBU for 0.2 to 2 hours.

Many of the silyl sulfonamides of Formula II can be prepared by reacting sulfonyl chlorides of Formula V with t-butyldimethylsilylamine (J. R. Bowser, et al., Inorganic Chemistry. 17. 1882 (1978)) as shown in Equation 3.

Equation 3:

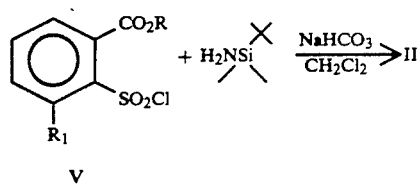

V

The reaction is carried out at 0° to 30° C. in a solvent such as dichloromethane in the presence of 1 to 2 equivalents of the amine and 1 equivalent of sodium bicarbonate.

Alternatively, many silyl sulfonamides of Formula II can be prepared by reacting silylsulfonamides of Formula VI with alkyl chloroformates as shown in Equation 4.

Equation 4:

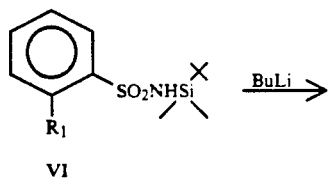

VI

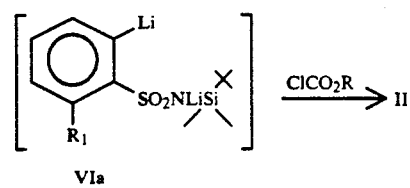

VIa

The reaction is carried out by contacting suitable silyl sulfonamides of Formula VI with an organolithium reagent such as n-butyllithium in an inert aprotic solvent such as tetrahydrofuran at −78° to 0° C. for 0.5 to 3 hours. The dilithio-intermediate VIa is then reacted with an alkyl orthoformate at −78° to 0° C. for 0.5 to 5 hours. Silylsulfonamides II are isolated by standard methods which are well known to one skilled in the art.

Many silyl sulfonamides of Formula II can be prepared by the indirect route shown in Equation 5.

Equation 5:

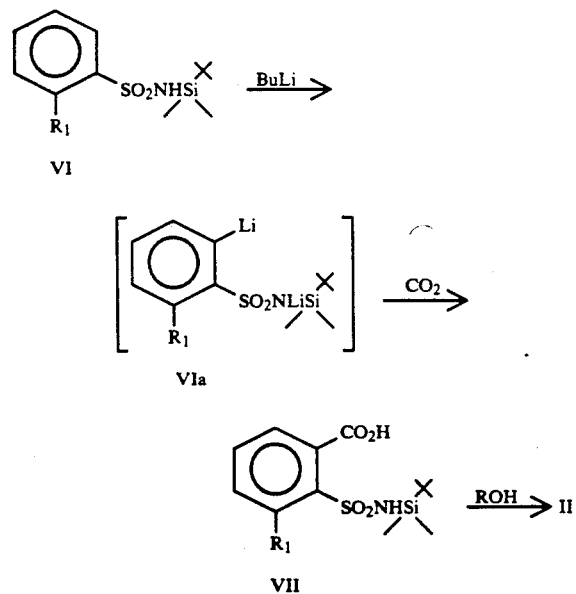

The first two steps are done as described above for Equation 4. J. G. Lombardino (*J. Org. Chem.*, 36, 1843 (1971)) also describes methods for preparing acid intermediate which are similar to acids of Formula VII. Methods to esterify acids under mild conditions are well known in the art.

Many sulfonamides of Formula IV can be prepared by deprotecting t-butylsulfonamides of Formula IIa as in Equation 6.

Equation 6:

IIa

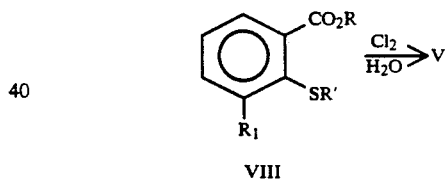

IV

The reaction is carried out at −78° to 30° C. in an inert solvent such as hexane in the presence of an acid such as trifluoroacetic acid. The success of this reaction depends on the nature of $R_1$ and R and will be known to one skilled in the art.

Sulfonamides of Formula IIa can be prepared by methods similar to those described in Equations 3, 4 and 5 in which the t-butyldimethylsilyl moiety has been replaced by the t-butyl moiety.

The sulfonyl chlorides of Formula V can be prepared by oxidatively chlorinating the corresponding sulfur-containing compounds of Formula VIII as shown in Equation 7. R ' is H, alkyl, benzyl or carbamoyl.

Equation 7:

VIII

The reaction of Equation 7 is carried out by contacting compounds of Formula VIII in a solvent such as acetic acid or proprionic acid with at least 3.0 equivalents of chlorine in the presence of at least 2.5 equivalents of water at about −20° to 30° C. for 0.2 to 5 hours. A. Wagenaar teaches specific reaction conditions for related compounds in *Recl. Trav. Chim. Pays-Bas* 101, 91 (1982).

Alternatively, reaction of compounds of Formula VIII, wherein R' is H or benzyl, with a hypochlorite solution such as 5% NaOCl can provide sulfonyl chlorides of Formula V. Reaction conditions for similar reactions are described in South African Patent Application No. 84/8845 and EP-A-142,152.

As shown in Equation 8, many of the sulfonyl chlorides of Formula V can be prepared from the corresponding amines of Formula IX by a Meerwein reaction.

Equation 8:

-continued

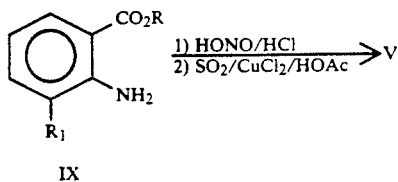

IX

The reaction involves diazotization of the amine IX with sodium nitrite in aqueous HCl, followed by reaction of the diazonium salt with sulfur dioxide and cupric chloride in acetic acid analogous to the teachings of Yale and Sowinski, *J. Org.. Chem.*, 25, 1824 (1960).

Alternatively, sulfonyl chlorides of Formula V can be prepared by a modification of the above procedure as shown in Equation 9.

Equation 9:

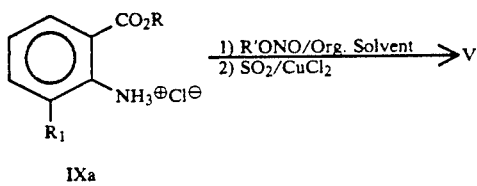

IXa

The amine hydrochloride salts IXa are diazotized with an alkyl nitrite in an organic solvent, such as acetonitrile or acetone, and the resulting diazonium salts are reacted with sulfur dioxide and cupric chloride to give sulfonyl chlorides. V. M. Doyle, in *J. Org. Chem.*, 42. 2426, 2431 (1977), describes conditions for doing similar Meerwein reactions.

The heterocyclic carbamates of Formula III in Equations 1 and 2 can be prepared by methods described in U.S. Pat. No. 4,744,816.

The preparation of compounds of this invention is further illustrated by the following examples.

EXAMPLE 1

3-Methyl-2-(phenylmethylthio)-benzoic acid, 1-methylethyl ester

To a stirred suspension of dry tetrahydrofuran (125mL) and 35% potassium hydride in oil (6.3 g) was slowly added benzyl mercaptan (6.1 mL) at 0° C. under an inert atmosphere. After 15 minutes, 3-methyl-2-nitrobenzoic acid, 1-methylethyl ester (11.23 g) was added and the resulting mixture was stirred at room temperature overnight. The reaction mixture was partitioned between 6N sodium hydroxide (25 mL) and ethyl acetate (150 mL). The organic phase was dried over magnesium sulfate, filtered, concentrated, and chromatographed on silica gel eluted with 5% ethyl acetate in hexanes to give 13.7 g of the title compound as a yellow oil, $n_D$ 1.5642.

90 MHz NMR (CDCl$_3$): δ 1 39 (d, 6H, CH$_3$); 2.39 (s, 3H, CH$_3$); 3.99 (s, 2H, CH$_2$); 5.32 (m, 1H, CH); and 7.26 (m, 8H, arom.).

IR (neat) 1720 cm$^{-1}$.

EXAMPLE 2

Methyl 2-(chlorosulfonyl)-3-methylbenzoate

To a stirred suspension of methyl 3-methyl-2-(Phenylmethylthio)-benzoate (24 g), dichloromethane (700 mL), water (150 mL), and concentrated hydrochloric acid (34 mL), kept at 0° C., was slowly added 5% sodium hypochlorite (450 mL). The resulting yellow suspension was stirred at 0° C. for 1 hour. The dichloromethane phase was dried over magnesium sulfate, filtered, concentrated, and triturated with chlorobutane-hexanes to give 14 g of the title compound as a white solid, m.p. 114-116° C.

90 MHz NMR (CDCl$_3$): δ 2.82 (s, 3H, CH$_3$); 3.97 (s, 3H, OCH$_3$); and 7.5 (m, 3H, arom.).

IR (nujol) 1730, 1360, and 1175 cm$^{-1}$.

EXAMPLE 3

Ethyl 2-[((dimethyl)-(1.1-dimethylethyl)silylamino)sulfonyl]-3-nitrobenzoate

A suspension of ethyl 2-(chlorosulfonyl)-3-nitrobenzoate (14.7 g), amino-t-butyldimethylsilane (15.4 g), and sodium bicarbonate (3.5 g) in dichloromethane (300 mL) was stirred at room temperature in a stoppered flask for 4 days. Water (90 mL) and saturated aqueous bicarbonate (45 mL) were added, and the mixture was stirred. The dichloromethane phase was dried over magnesium sulfate, filtered, concentrated, and chromatographed on silica gel eluted with 20% ethyl acetate in hexanes to give 12.9 g of the title compound as a white solid, m.p. 101-102° C.

90 MHz NMR (CDCl$_3$): δ 0.30 (s, 6H, SiCH$_3$); 0.97 (s, 9H, CH$_3$); 1.41 (t, 3H, CH$_3$); 4.48 (q, 2H, OCH$_2$); 5.86 (s, 1H, NH); and 7.7 (m, 3H, arom.).

IR (nujol) 3200, 1730 and 1700 cm$^{-1}$.

EXAMPLE 4

Methyl 2-[((dimethyl)-1,1-dimethylethyl)silylamino)sulfonyl]-3-trifluoromethylbenzoate A solution of N-[(dimethyl)-(1,1-dimethylethyl)silyl]-2-trifluoromethylbenzenesulfonamide (17.5 g) in dry tetrahydrofuran (250 mL) was contacted with 2.5 M butyllithium (46 mL) at 50° C. and allowed to warm to 0° C. over 1.5 hours under an inert atmosphere. The mixture was cooled to −78° C. and added to a solution of methyl chloroformate in dry tetrahydrofuran (300 mL) at −78° C. The mixture was stirred at −78° C. under an inert atmosphere for 1.5 hours and then quenched with saturated aqueous ammonium chloride (100 mL). After warming to 0° C., the tetrahydrofuran layer was dried over magnesium sulfate, filtered, evaporated, and chromatographed on silica gel eluted with 20% chlorobutane, 10% tetrahydrofuran and 70% hexanes to give 2.13 g of the title compound as a white solid, m.p. 80-84° C.

MHz NMR (CDCl$_3$): δ0.29 (s, 6H, SiCH$_3$); 0.96 (s, 9H, CH$_3$); 4.02 (s, 3H, OCH$_3$); 5.63 (s, 1H, NH); 7.8 (m, 2H, arom:); and 8 (m, 1H, arom.).

IR (nujol) 3250, 1725 cm$^{-1}$

EXAMPLE 5

Ethyl 2-[[[[[4-(dimethylamino)-6-(2,2,2-trifluoroethoxy)-1,3,5-triazin-2-yl]amino]carbonyl]amino]sulfonyl]-3-methylbenzoate A solution of 2-(dimethyl-(1,1-dimethylethyl)-silylamino)-3-methylbenzoic acid, ethyl ester (0.36 g) and 0-phenyl-N-[4-dimethylamino-6-(2,2,2-trifluoroethoxy)-1,3,5-triazin-2-yl]carbamate (0.39 g) in acetonitrile (10 mL) was treated with 1M tetrabutylammonium fluoride in tetrahydrofuran (1.1 mL). The mixture was stirred for 2 hours. After diluting the reaction with water (20 mL) and acidifying with 1N hydrochloric acid, the resulting precipitate was filtered, washed with water and hexane/ether, and air dried to give 0.28 g of the title compound as a white solid, m.p. 134–142° C.

200 MHz NMR (CDCl$_3$): δ 6 1.38 (t, 3H, CH$_3$); 2.89 (s, 3H, CH$_3$); 3.24 (s, 6H, NCH$_3$); 4.36 (q, 2H, OCH$_2$); 4.74 (q, 2H, CH$_2$); 7.4 (m, 4H, arom. and NH); and 12.38 (s, 1H, NH).

IR (nujol) 1710, 1695 cm$^{-1}$.

EXAMPLE 6

Methyl 2-[[[[[4-(dimethylamino)-6-(2,2,2-trifluoroethoxy)-1,3,5-triazin-2-yl]amino]carbonyl]amino]sulfonyl]-3-methylbenzoate A solution of methyl 2-(dimethyl-(1,1-dimethylethyl)silylamino)-3-methylbenzoate (0.68 g) and -phenyl-N-[4-dimethylamino-6-(2,2,2-trifluoroethoxy)-1,3,5-triazin-2-yl]carbamate (0.79 g) in tetrahydrofuran (10 mL) was treated with 1M tetrabutylammonium fluoride in tetrahydrofuran (2.2 mL). The mixture was stirred for 1 hour. After diluting the reaction with water (30 mL) and acidifying with 1N hydrochloric acid, the resulting precipitate was filtered, washed with water and chlorobutane/hexane, and air dried to give 0.58 g of the title compound as a white solid, m.p. 151–159° C. with decomposition. Another sample previously prepared by this method melted at 150–160° C. with decomposition.

300 MHz NMR (DMSO): δ6 3.04 (s, 3H, CH$_3$); 3.46 (s, 6H, NCH$_3$); 4.10 (s, 3H, OCH$_3$); 5.32 (m, 2H, CH$_2$); 7.78 (d, 1H, arom.); 7.84 (d, 1H, arom.); 7.98 (m, 1H, arom.); 11.1 (s, 1H, NH); and 13.1 (s, 1H, NH).

IR (nujol) 1730 cm$^{-1}$.

The following compounds may be prepared by one skilled in the art using the general methods described earlier and exemplified in Examples 1 to 6.

TABLE 1

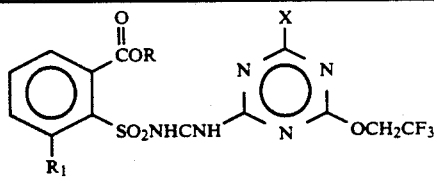

| R$_1$ | R | X |
|---|---|---|
| CH$_3$ | CH$_3$ | NHCH$_3$ |
| CH$_3$ | CH$_3$ | N(CH$_3$)$_2$ |
| CH$_3$ | CH$_2$CH$_3$ | NHCH$_3$ |
| CH$_3$ | CH$_2$CH$_3$ | N(CH$_3$)$_2$ |
| CH$_3$ | CH$_2$CH$_2$CH$_3$ | NHCH$_3$ |
| CH$_3$ | CH$_2$CH$_2$CH$_3$ | N(CH$_3$)$_2$ |
| CH$_3$ | CH(CH$_3$)$_2$ | NHCH$_3$ |
| CH$_3$ | CH(CH$_3$)$_2$ | NHCH$_3$ |
| CH$_3$ | CH$_2$CH$_2$CH$_2$CH$_3$ | NHCH$_3$ |
| CH$_3$ | CH$_2$CH$_2$CH$_2$CH$_3$ | N(CH$_3$)$_2$ |
| CH$_3$ | CH$_2$CH(CH$_3$)$_2$ | NHCH$_3$ |
| CH$_3$ | CH$_2$CH(CH$_3$)$_2$ | N(CH$_3$)$_2$ |
| CH$_3$ | CH(CH$_3$)CH$_2$CH$_3$ | NHCH$_3$ |
| CH$_3$ | CH(CH$_3$)CH$_2$CH$_3$ | N(CH$_3$)$_2$ |
| CH$_3$ | CH$_2$CH=CH$_2$ | NHCH$_3$ |
| CH$_3$ | CH$_2$CH=CH$_2$ | N(CH$_3$)$_2$ |
| CH$_3$ | CH$_2$C≡CH | NHCH$_3$ |
| CH$_3$ | CH$_2$C≡CH | N(CH$_3$)$_2$ |
| CH$_3$ | CH$_2$-cyclopropyl | NHCH$_3$ |

TABLE 1-continued

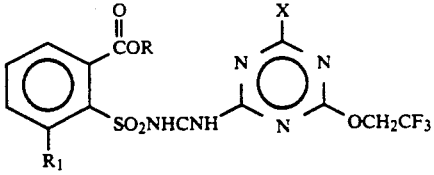

| R$_1$ | R | X |
|---|---|---|
| CH$_3$ | CH$_2$-cyclopropyl | N(CH$_3$)$_2$ |
| CH$_3$ | CH$_2$CH$_2$OCH$_3$ | NHCH$_3$ |
| CH$_3$ | CH$_2$CH$_2$OCH$_3$ | N(CH$_3$)$_2$ |
| CH$_3$ | CH$_2$CH$_2$OCH$_2$CH$_3$ | N(CH$_3$)$_2$ |
| CH$_3$ | CH$_2$CH$_2$SCH$_3$ | NHCH$_3$ |
| CH$_3$ | CH$_2$CH$_2$SCH$_3$ | N(CH$_3$)$_2$ |
| CH$_3$ | CH$_2$CH$_2$SCH$_2$CH$_3$ | NHCH$_3$ |
| CH$_3$ | CH$_2$CH$_2$CN | NHCH$_3$ |
| CH$_3$ | CH$_2$CH$_2$CN | N(CH$_3$)$_2$ |
| CH$_3$ | CH$_2$CH$_2$Cl | N(CH$_3$)$_2$ |
| CH$_3$ | CH$_2$CH$_2$F | N(CH$_3$)$_2$ |
| CH$_3$ | CH$_2$CH$_2$Br | N(CH$_3$)$_2$ |
| CH$_2$CH$_3$ | CH$_3$ | N(CH$_3$)$_2$ |
| CH$_2$CH$_3$ | CH$_3$ | NHCH$_3$ |
| CH$_2$CH$_3$ | CH$_2$CH$_3$ | NHCH$_3$ |
| CH$_2$CH$_3$ | CH$_2$CH$_3$ | N(CH$_3$)$_2$ |
| CH$_2$CH$_3$ | CH(CH$_3$)$_2$ | N(CH$_3$)$_2$ |
| CH$_2$CH$_3$ | CH$_2$CH=CH$_2$ | N(CH$_3$)$_2$ |
| CH$_2$CH$_3$ | CH$_2$CH$_2$Cl | N(CH$_3$)$_2$ |
| CF$_3$ | CH$_3$ | N(CH$_3$)$_2$ |
| CF$_3$ | CH$_3$ | NHCH$_3$ |
| CF$_3$ | CH$_2$CH$_3$ | NHCH$_3$ |
| CF$_3$ | CH$_2$CH$_3$ | N(CH$_3$)$_2$ |
| CF$_3$ | CH$_2$-cyclopropyl | N(CH$_3$)$_2$ |
| CF$_3$ | CH$_2$-cyclopropyl | NHCH$_3$ |
| CF$_3$ | CH$_2$CN | NHCH$_3$ |
| CH$_2$CH$_2$Cl | CH$_3$ | NHCH$_3$ |
| CH$_2$CH$_2$Cl | CH$_2$CH$_3$ | NHCH$_3$ |
| CH$_2$CH$_2$Cl | CH$_2$CH$_2$CH$_2$CH$_3$ | NHCH$_3$ |
| CH$_2$CN | CH$_3$ | NHCH$_3$ |
| CH$_2$CN | CH$_3$ | N(CH$_3$)$_2$ |
| CH$_2$CN | CH$_2$CH$_3$ | N(CH$_3$)$_2$ |
| CH$_2$CN | CH$_2$CH$_3$ | NHCH$_3$ |
| CH$_2$CN | CH$_2$CH$_2$CH$_3$ | NHCH$_3$ |
| CH$_2$CN | CH$_2$CH$_2$CH$_2$CH$_3$ | NHCH$_3$ |
| CH$_2$CN | CH$_2$CH=CH$_2$ | NHCH$_3$ |
| CH$_2$CN | CH$_2$CH=CH$_2$ | N(CH$_3$)$_2$ |
| CH$_2$CN | CH$_2$CH$_2$OCH$_2$CH$_3$ | N(CH$_3$)$_2$ |
| CH$_2$CN | CH$_2$CH$_2$OCH$_2$CH$_3$ | NHCH$_3$ |
| CH$_2$OCH$_3$ | CH$_2$CH$_3$ | NHCH$_3$ |
| CH$_2$OCH$_3$ | CH$_2$CH$_3$ | N(CH$_3$)$_2$ |
| CH$_2$OCH$_3$ | CH(CH$_3$)$_2$ | N(CH$_3$)$_2$ |
| CH$_2$OCH$_3$ | CH(CH$_3$)$_2$ | NHCH$_3$ |
| CH$_2$OCH$_3$ | CH$_2$-cyclopropyl | NHCH$_3$ |
| CH$_2$OCH$_3$ | CH$_2$-cyclopropyl | N(CH$_3$)$_2$ |
| OCH$_3$ | CH$_3$ | N(CH$_3$)$_2$ |
| OCH$_3$ | CH$_3$ | NHCH$_3$ |
| OCH$_3$ | CH$_2$CH$_3$ | NHCH$_3$ |
| OCH$_3$ | CH$_2$CH$_3$ | N(CH$_3$)$_2$ |
| OCH$_3$ | CH(CH$_3$)$_2$ | N(CH$_3$)$_2$ |
| OCH$_3$ | CH(CH$_3$)$_2$ | NHCH$_3$ |
| OCH$_3$ | CH$_2$CH=CH$_2$ | NHCH$_3$ |
| OCH$_3$ | CH$_2$CH=CH$_2$ | N(CH$_3$)$_2$ |

TABLE 1-continued

| R₁ | R | X |
|---|---|---|
| OCH₃ | CH₂—△ | N(CH₃)₂ |
| OCH₃ | CH₂CH₂OCH₂CH₃ | N(CH₃)₂ |
| OCH₃ | CH₂CH₂SCH₃ | N(CH₃)₂ |
| OCH₃ | CH₂CH₂SCH₂CH₃ | N(CH₃)₂ |
| OCH₃ | CH₂CH₂CN | N(CH₃)₂ |
| OCH₂CH₃ | CH₂CH₃ | NHCH₃ |
| OCH₂CH₃ | CH₂CH₃ | N(CH₃)₂ |
| OCH₂CH₃ | CH₂CH₂OCH₃ | NHCH₃ |
| OCH₂CH₃ | CH₂CH₂Br | NHCH₃ |
| OCH₂CH₂CH₃ | CH₃ | N(CH₃)₂ |
| OCH₂CH₂CH₃ | CH₂CH₃ | N(CH₃)₂ |
| OCH(CH₃)₂ | CH₃ | N(CH₃)₂ |
| OCH(CH₃)₂ | CH₂CH₃ | N(CH₃)₂ |
| OCH(CH₃)₂ | CH₂CH₂OCH₃ | N(CH₃)₂ |
| SCH₃ | CH₃ | NHCH₃ |
| SCH₃ | CH₃ | N(CH₃)₂ |
| SCH₃ | CH₂CH₃ | N(CH₃)₂ |
| SCH₃ | CH₂CH₃ | NHCH₃ |
| SCH₃ | CH₂CH₂CH₃ | NHCH₃ |
| SCH₃ | CH₂C≡CH | NHCH₃ |
| SCH₃ | CH₂CH₂OCH₃ | NHCH₃ |
| SCH₂CH₃ | CH₃ | NHCH₃ |
| SCH₂CH₃ | CH₃ | N(CH₃)₂ |
| SCH₂CH₃ | CH₂CH₃ | N(CH₃)₂ |
| SCH₂CH₃ | CH₂CH₃ | NHCH₃ |
| SCH₂CH₃ | CH₂—△ | NHCH₃ |
| SCH₂CH₃ | CH₂—△ | NH(CH₃)₂ |
| SCH₂CH₃ | CH₂CH₂SCH₃ | N(CH₃)₂ |
| SCH₂CH₃ | CH₂CH₂OCH₃ | N(CH₃)₂ |
| SCH₂CH₂CH₃ | CH₃ | N(CH₃)₂ |
| SCH₂CH₂CH₃ | CH₂CH₃ | N(CH₃)₂ |
| SCH₂CH₂CH₃ | CH₂CH₂Br | N(CH₃)₂ |
| SCH(CH₃)₂ | CH₃ | N(CH₃)₂ |
| SCH(CH₃)₂ | CH₂CH₂OCH₃ | N(CH₃)₂ |
| SCH(CH₃)₂ | CH₂—△ | N(CH₃)₂ |
| SC₆H₅ | CH₃ | NHCH₃ |
| SC₆H₅ | CH₃ | N(CH₃)₂ |
| SC₆H₅ | CH₂CH₃ | NHCH₃ |
| SC₆H₅ | CH₂CH₃ | N(CH₃)₂ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101-103.

In the following Examples, all parts are by weight unless otherwise indicated.

EXAMPLE 7

Wettable Powder

| Wettable Powder | |
| --- | --- |
| Methyl 2-[[[[[4-(dimethylamino)-6-(2,2,2-trifluoro-ethoxy)-1,3,5-triazin-2-yl]amino]carbonyl]amino]sulfonyl]-3-methylbenzoate | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 8

| Wettable Powder | |
| --- | --- |
| Ethyl 2-[[[[[4-(dimethylamino)-6-(2,2,2-trifluoro-ethoxy)-1,3,5-triazin-2-yl]amino]carbonyl]amino]sulfonyl]-3-methylbenzoate | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 9

| Granule | |
| --- | --- |
| Wettable Powder of Example 8 | 5% |
| attapulgite granules (U.S.S. 20 to 40 mesh; 0.84–0.42 mm) | 95% |

A slurry of wettable powder containing 25% solids is sprayed on the surface of attapulgite granules in a double-cone blender. The granules are dried and packaged.

EXAMPLE 10

| Extruded Pellet | |
| --- | --- |
| Methyl 2-[[[[[4-(dimethylamino)-6-(2,2,2-trifluoro-ethoxy)-1,3,5-triazin-2-yl]amino]carbonyl]amino]sulfonyl]-3-methylbenzoate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

| Low Strength Granule | |
| --- | --- |
| Ethyl 2-[[[[[4-(dimethylamino)-6-(2,2,2-trifluoro-ethoxy)-1,3,5-triazin-2-yl]amino]carbonyl]amino]sulfonyl]-3-methylbenzoate | 0.1% |
| attapulgite granules (U.S.S. 20 to 40 mesh, 0.42 to 0.84 mm) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 12

| Granule | |
| --- | --- |
| Methyl 2-[[[[[4-(dimethylamino)-6-(2,2,2-trifluoro-ethoxy)-1,3,5-triazin-2-yl]amino]carbonyl]amino]sulfonyl]-3-methylbenzoate | 80% |
| wetting agent | 1% |
| crude ligninsulfonate salt (containing 5 to 20% of the natural sugars) | 10% |
| attapulgite clay | 9% |

The ingredients are blended and milled to Pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14 to 100 mesh (1410 to 149 microns), and packaged for use.

EXAMPLE 13

| Low Strength Granule | |
| --- | --- |
| Ethyl 2-[[[[[4-(dimethylamino)-6-(2,2,2-trifluoro-ethoxy)-1,3,5-triazin-2-yl]amino]carbonyl]amino]sulfonyl]-3-methylbenzoate | 1% |
| N,N-dimethylformamide | 9% |
| attapulgite granules (U.S.S. 20 to 40 sieve, 0.42 to 0.84 mm) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 14

| Aqueous Suspension | |
| --- | --- |
| Methyl 2-[[[[[4-(dimethylamino)-6-(2,2,2-trifluoro-ethoxy)-1,3,5-triazin-2-yl]amino]carbonyl]amino]sulfonyl]-3-methylbenzoate | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |

-continued

| Aqueous Suspension | |
|---|---|
| water | 56.7% |

The ingredients are blended and ground together in a sand mill to produce particles essentially all under 5 microns in size.

EXAMPLE 15

| Solution | |
|---|---|
| Ethyl 2-[[[[[4-(dimethylamino)-6-(2,2,2-trifluoro-ethoxy)-1,3,5-triazin-2-yl]amino]carbonyl]amino]sulfonyl]-3-methylbenzoate, sodium salt | 5% |
| water | 95% |

The salt is added directly to the water with stirring to produce the solution, which may then be packaged for use.

EXAMPLE 16

| High Strength Concentrate | |
|---|---|
| Methyl 2-[[[[[4-(dimethylamino)-6-(2,2,2-trifluoro-ethoxy)-1,3,5-triazin-2-yl]amino]carbonyl]amino]sulfonyl]-3-methylbenzoate | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 17

| Wettable Powder | |
|---|---|
| Ethyl 2-[[[[[4-(dimethylamino)-6-(2,2,2-trifluoro-ethoxy)-1,3,5-triazin-2-yl]amino]carbonyl]amino]sulfonyl]-3-methylbenzoate | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 18

| Wettable Powder | |
|---|---|
| Methyl 2-[[[[[4-(dimethylamino)-6-(2,2,2-trifluoro-ethoxy)-1,3,5-triazin-2-yl]amino]carbonyl]amino]sulfonyl]-3-methylbenzoate | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 19

| Oil Suspension | |
|---|---|
| Ethyl 2-[[[[[4-(dimethylamino)-6-(2,2,2-trifluoro- | 35% |

-continued

| Oil Suspension | |
|---|---|
| ethoxy)-1,3,5-triazin-2-yl]amino]carbonyl]amino]sulfonyl]-3-methylbenzoate | |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 20

| Dust | |
|---|---|
| Methyl 2-[[[[[4-(dimethylamino)-6-(2,2,2-trifluoro-ethoxy)-1,3,5-triazin-2-yl]amino]carbonyl]amino]sulfonyl]-3-methylbenzoate | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 21

| Oil Suspension | |
|---|---|
| Ethyl 2-[[[[[4-(dimethylamino)-6-(2,2,2-trifluoro-ethoxy)-1,3,5-triazin-2-yl]amino]carbonyl]amino]sulfonyl]-3-methylbenzoate | 25% |
| Polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 22

| Wettable Powder | |
|---|---|
| Methyl 2-[[[[[4-(dimethylamino)-6-(2,2,2-trifluoro-ethoxy)-1,3,5-triazin-2-yl]amino]carbonyl]amino]sulfonyl]-3-methylbenzoate | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Utility

The compounds of this invention are particularly useful for the control of undesired vegetation in sugar beets, fodder beets, and red beets. These are crops that take long time periods to become established. In this interval, the crop seedlings must be nurtured carefully, with particular attention to weed control to prevent damage and yield loss due to competition. The subject compounds can be used either pre- or post-emergence and will control numerous problem weeds including catchweed bedstraw (*Galium aparine*) wild buckwheat (*Polygonum convolvulus*), wild mustard (*Sinapsis arvensis*) and blackgrass (*Alopercurus mysoroides*).

The rate of application for these compounds is determined by a number of factors including the weeds to be controlled, weather and climate, soil type, time of application, age and size of crop and weeds, method of application, etc. In general terms, the rate will vary between about 0.5 and 1000 g/ha, with preferred rates of about 10 to 125 g/ha. The rate to be used in any given situation can be selected by one with ordinary skill in the art.

These compounds can and will often be used in mixtures with one or more other herbicides. They may be mixed with other herbicides selective on beet crops, including metamitron, phenmedipham, desmedipham, chloridazon, lenacil, ethofumesate, cycloate, clopyralid, diallate, triallate, diclofop-methyl, quizalofop-ethyl, fuzalifop-butyl, haloxafop, sethoxidym and alloxidym.

The selective properties of these compounds were discovered in greenhouse tests. The results of these tests clearly show the activity and selectivity of these compounds and are shown in the tables below.

COMPOUNDS

| CMPD | R₁ | R | X | m.p. (°C.) |
|---|---|---|---|---|
| 1 | CH₃ | CH₂CH₃ | N(CH₃)₂ | 134–142 |
| 2 | CH₃ | CH₃ | NHCH₃ | 123–129(d) |
| 3 | CH₃ | CH₃ | N(CH₃)₂ | 150–160(d) |
| 4 | CH₃ | (CH₂)₂CH₃ | N(CH₃)₂ | 143–150(d) |
| 5 | CH₃ | (CH₂)₂CH₃ | NHCH₃ | 159–163 |
| 6 | CH₃ | CH(CH₃)₂ | NHCH₃ | 185–186 |
| 7 | CH₃ | CH(CH₃)₂ | N(CH₃)₂ | 155–156 |
| 8 | CH₃ | CH₂-cyclo-C₃H₅ | N(CH₃)₂ | 105–115(d) |

-continued
COMPOUNDS

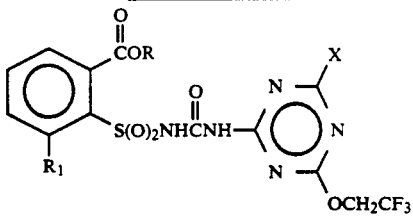

| CMPD | R₁ | R | X | m.p. (°C.) |
|---|---|---|---|---|
| 9 | CH₃ | CH₂CH₃ | NHCH₃ | 149–152 |
| 10 | CH₃ | C(CH₃)₃ | NHCH₃ | 181–183 |
| 11 | CH₃ | C(CH₃)₃ | N(CH₃)₂ | 82–89 |

TEST A

Seeds of barley (*Hordeum vulgare*), barnyardgrass (*Echinochloa crus-galli*), cheatgrass (*Bromus secalinus*) or downy brome (*Bromus tectorum*), cocklebur (*Xanthium pensylvanicum*), corn (*Zea mays*), cotton (*Gossypium hirsutum*), crabgrass (*Digitaria* spp.), giant foxtail (*Setaria faberi*), morningglory (*Ipomoea* spp.), rice (*Oryz sativa*), sorghum (*Sorghum bicolor*), soybean (*Glycine max*), sugar beet (*Beta vulgaris*), velvetleaf (*Abutilon theophrasti*), wheat (*Triticum aestivum*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated Plants and controls were maintained in a greenhouse for sixteen days, after which all species were compared to controls and visually evaluated. The ratings, summarized in Table A, are based on a scale of 0 to 10 where 0 is no effect and 10 is complete control. A dash (—) response means no test. The accompanying descriptive symbols have the following meanings:

C=chlorosis/necrosis;
G=growth retardation; and
H=formative effect.

TABLE A

| | POSTEMERGENCE | | | | | | | | | |
|---|---|---|---|---|---|---|---|---|---|---|
| | Cmpd 1 | | 2 | | 3 | | 4 | | 5 | |
| RATE (g/ha) | 50 | 10 | 50 | 10 | 50 | 10 | 50 | 10 | 50 | 10 |
| Barley | 3C, 9G | 8G | 3C, 9G | 3C, 9G | 2C, 9G | 3C, 9G | 8G | 4G | 9G | 7G |
| Barnyardgrass | 9C | 3C, 9H | 9C | 3C, 9G | 9C | 4C, 9H | 3C, 7H | 3C, 6G | 3C, 7G | 3C, 5G |
| Cheatgrass | — | — | 2C, 9G | 3C, 8G | 5C, 9G | 4C, 9G | 4G | 0 | 3C, 9G | 0 |
| Cocklebur | 10C | 3C, 9H | 9C | 3C, 7H | 10C | 4C, 9G | 4C, 9G | 2C, 7G | 3C, 8G | 2C, 7G |
| Corn | 3C, 9G | 3C, 9G | 3C, 9G | 3C, 9H | 9G | 3C, 9H | 3C, 7H | 3G | 3C, 5G | 4G |
| Cotton | 9G | 3C, 6G | 5C, 9G | 4C, 9H | 4C, 9G | 4C, 9H | 3C, 8H | 8H | 4C, 9H | 3C, 8H |
| Crabgrass | 0 | 0 | 3C, 7G | 3G | 3C, 8G | 2C, 4G | 0 | 0 | 2G | 0 |
| Downy brome | 5C, 9G | 3C, 9G | — | — | — | — | — | — | — | — |
| Giant foxtail | 3C, 7G | 2G | 3C, 9G | 3C, 7G | 3C, 9G | 3C, 6G | 2G | 0 | 5G | 2G |
| Morningglory | 10C | 4C, 9H | 9C | 5C, 9G | 9C | 4C, 8H | 5C, 9G | 4C, 8H | 5C, 9G | 3C, 8H |
| Nutsedge | 5G | — | 2C, 9G | — | 9C | 9C | 0 | 0 | — | 0 |
| Rice | 9C | 5C, 9G | 9C | 9C | 5C, 9G | 5C, 9G | 3C, 7G | 2G | 3C, 7G | 5G |
| Sorghum | 4C, 9G | 9H | 5C, 9G | 5C, 9G | 5C, 9G | 4C, 9G | 2C, 3G | 2G | 2C, 5G | 2G |
| Soybean | 4C, 9G | 4C, 9G | 9C | 4C, 9G | 4C, 9G | 4C, 9G | 3C, 8H | 3C, 4G | 4C, 9G | 4C, 8H |
| Sugar beet | 0 | 0 | 2G | 0 | 4G | 0 | 0 | 0 | 3G | 0 |
| Velvetleaf | 9C | 4C, 8H | 10C | 3C, 8G | 10C | 4C, 9G | 2C, 8H | 2G | 8G | 2C, 6G |
| Wheat | 4C, 9G | 7G | 9G | 9G | 3C, 9G | 9G | 3G | 0 | 4G | 2G |
| Wild oat | 4C, 9G | 3C, 6G | 3C, 8G | 3C, 5G | 3C, 8G | 3C, 5G | 3G | 0 | 3C, 4G | 1C |

| | POSTEMERGENCE | | | | | | | |
|---|---|---|---|---|---|---|---|---|
| | 6 | | 7 | | 8 | | 9 | |
| RATE (g/ha) | 50 | 10 | 50 | 10 | 50 | 10 | 50 | 10 |

TABLE A-continued

| | | | | | | | | |
|---|---|---|---|---|---|---|---|---|
| Barley | 4C, 9G | 3C, 8H | 9G | 7G | 4G | 0 | 9G | 8G |
| Barnyardgrass | 3C, 9H | 3C, 7H | 3C, 8H | 2C, 6H | 2C, 4G | 0 | 9G | 3C, 7H |
| Cheatgrass | 7G | 6G | 7G | 4G | 0 | 0 | 9G | 3G |
| Cocklebur | 3C, 8H | 3C, 8H | 5C, 9G | 3C, 8G | 3C, 4G | 1C, 2G | 4C, 9G | 4C, 7H |
| Corn | 3C, 8H | 3C, 8G | 3C, 9G | 2C, 7G | 2C, 4G | 0 | 3C, 9H | 3C, 6G |
| Cotton | 4C, 9G | 9H | 3C, 9G | 3G | 1C, 3G | 0 | 4C, 8G | 3C, 7G |
| Crabgrass | 3G | 0 | 0 | 0 | 0 | 0 | 6G | 3G |
| Downy brome | — | — | — | — | — | — | — | — |
| Giant foxtail | 3G | 0 | 2G | 0 | 0 | 0 | 7G | 3G |
| Morningglory | 4C, 9G | 3C, 8H | 3C, 9G | 3C, 8G | 3C, 6G | 2C | 9C | 4C, 8G |
| Nutsedge | — | — | — | — | 0 | 0 | 9G | 4G |
| Rice | 4C, 8G | 3C, 7G | 3C, 8G | 2C, 3G | 2C, 2G | 0 | 5C, 9G | 5C, 9G |
| Sorghum | 4C, 9G | 4C, 9G | 3C, 8H | 3C, 8G | 6G | 0 | 9G | 9G |
| Soybean | 5C, 9H | 4C, 8G | 4C, 9G | 4C, 8G | 3C, 4G | 0 | 5C, 9G | 5C, 9G |
| Sugar beet | 1H | 0 | 0 | 0 | 0 | 0 | 0 | 0 |
| velvetleaf | 2C, 8H | 2C, 5G | 3C, 8H | 0 | 0 | 0 | 9C | 4C, 9G |
| Wheat | 8G | 6G | 8G | 7G | 3G | 0 | 9G | 9G |
| Wild oat | 9G | 3C, 7G | 2C, 6G | 2C, 5G | 0 | 0 | 3C, 9G | 7G |

PREEMERGENCE

| | Cmpd 1 | | 2 | | 3 | | 4 | | 5 | | 6 | |
|---|---|---|---|---|---|---|---|---|---|---|---|---|
| RATE (g/ha) | 50 | 10 | 50 | 10 | 50 | 10 | 50 | 10 | 50 | 10 | 50 | 10 |
| Barley | 9G | 0 | 3C, 8G | 3C, 8G | 9G | 4G | 2G | 0 | 8G | 3G | 8G | 2G |
| Barnyardgrass | 2G | 0 | 3C, 8H | 7H | 3C, 8H | 1H | 3G | 0 | 6G | 0 | 3C, 7H | 3G |
| Cheatgrass | — | — | 8G | 4G | 3C, 8H | 0 | 0 | 0 | 6G | 0 | 3C, 7G | 5G |
| Cocklebur | 3C, 4H | 0 | 4G | 0 | 2C, 2H | 0 | 3G | 0 | 8G | 2H | 3C, 5H | 3G |
| Corn | 3C, 7G | 2G | 4C, 9H | 3C, 3G | 4C, 9H | 4G | 3G | 0 | 3C, 7G | 3G | 3C, 8G | 3C, 7G |
| Cotton | 0 | 0 | 0 | 2G | 2G | 0 | 5G | 0 | 2G | 0 | 3G | 0 |
| Crabgrass | 0 | 0 | 3C, 5G | 2G | 3C, 6G | 4G | 0 | 0 | 2G | 0 | 3C, 7G | 2G |
| Downy brome | 5G | 0 | — | — | — | — | — | — | — | — | — | — |
| Giant foxtail | 2G | 0 | 3C, 7H | 5G | 2C, 3G | 0 | 0 | 0 | 2G | 0 | 2C, 7G | 2G |
| Morningglory | 3C, 3H | 0 | 4C, 9G | 5G | 3C, 4H | 0 | 2G | 0 | 7G | 3G | 9H | 3G |
| Nutsedge | 0 | 0 | 3C, 3G | 0 | 4G | 0 | 7G | 0 | 0 | 0 | 9G | 0 |
| Rice | 3C, 5G | 0 | 5C, 9H | 4G | 7G | 4G | 2G | 0 | 7G | 2G | 4G | 0 |
| Sorghum | 3C, 7G | 0 | 4C, 9H | 3C, 7G | 4C, 9H | 2C, 5G | 3G | 0 | 3C, 7G | 2G | 3C, 8H | 3C, 5G |
| Soybean | 2C, 2H | 1C | 4C, 6H | 3C, 3G | 3H | 2G | 3G | 0 | 3C, 5G | 3G | 3C, 6H | 2H |
| Sugar beet | 0 | 0 | 4G | 0 | 0 | 0 | 2G | 0 | 0 | 0 | 0 | 0 |
| Velvetleaf | 2H | 0 | 4H | 0 | 5H | 0 | 3G | 0 | 6G | 0 | 6H | 2G |
| Wheat | 4G | 0 | 2C, 8G | 3G | 8G | 0 | 0 | 0 | 4G | 0 | 2C, 3G | 0 |
| Wild oat | 2C, 5G | 0 | 2G | 0 | 2G | 0 | 0 | 0 | 5G | 0 | 6G | 3G |

PREEMERGENCE

| | | 7 | | 8 | | 9 | |
|---|---|---|---|---|---|---|---|
| | RATE (g/ha) | 50 | 10 | 50 | 10 | 50 | 10 |
| | Barley | 2C, 5G | 0 | 0 | 0 | 8G | 8G |
| | Barnyardgrass | 3C, 7G | 0 | 0 | 0 | 3C, 7H | 2G |
| | Cheatgrass | 6G | 0 | 0 | 0 | 6G | 0 |
| | Cocklebur | 7H | 0 | 0 | 0 | 3C, 7H | 0 |
| | Corn | 3C, 8G | 2C, 4G | 0 | 0 | 3C, 9G | 3C, 4G |
| | Cotton | 2G | 0 | 0 | 0 | 0 | 0 |
| | Crabgrass | 5G | 0 | 0 | 0 | 0 | 0 |
| | Downy brome | — | — | — | — | — | — |
| | Giant foxtail | 4G | 0 | 2G | 0 | 5G | 2G |
| | Morningglory | 8H | 0 | 0 | 0 | 9G | 3C, 4G |
| | Nutsedge | 0 | 0 | 0 | 0 | 0 | 0 |
| | Rice | 4G | 0 | 0 | 0 | 2C, 5G | 2G |
| | Sorghum | 3C, 8G | 2C, 2G | 0 | 0 | 4C, 9G | 2C, 4H |
| | Soybean | 2C, 4H | 2C, 2G | 0 | 0 | 4C, 8H | 2G |
| | Sugar beet | 0 | 0 | 0 | 0 | 0 | 0 |
| | Velvetleaf | 7H | 0 | 2H | 0 | 6H | 3H |
| | Wheat | 2G | 0 | 0 | 0 | 8G | 2G |
| | Wild oat | 6G | 0 | 0 | 0 | 7G | 2G |

TEST B

Seeds of barley (*Hordeum vulgare*), barnyardgrass (*Echinochloa crus-galli*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria* spp.), downy brome (*Bromus tectorum*), giant foxtail (*Setaria faberi*), green foxtail (*Setaria viridis*), jimsonweed (*Datura stramonium*), johnsongrass (*Sorghum halepense*), lambsquarters (*Chenopodium album*), morningglory (*Ipomoea* spp.), rape (*Brassica napus*), rice (*Oryza sativa*), sicklepod (*Cassia obtusifolia*), soybean (*Glycine max*), sugar beet (*Beta vulgaris*), teaweed (*Sida spinosa*), velvetleaf (*Abutilon theophrasti*), wheat (*Titicum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately 24 days, after which all species were compared to controls and visually evaluated. The ratings, summarized in Table B, are based on a scale of 0 to 100 where 0 is no effect and 100 is complete control. A dash (—) response means no test.

TABLE B

POSTEMERGENCE

| | Cmpd 1 | | | | 2 | | | | 3 | | | | 4 | | | | 5 | | | |
|---|---|---|---|---|---|---|---|---|---|---|---|---|---|---|---|---|---|---|---|---|
| RATE (g/ha) | 250 | 62 | 16 | 4 | 250 | 62 | 16 | 4 | 250 | 62 | 16 | 4 | 62 | 16 | 4 | 1 | 250 | 62 | 16 | 4 |
| Barley | 100 | 80 | 60 | 30 | 90 | 90 | 80 | 30 | 90 | 90 | 60 | 40 | 60 | 30 | 0 | 0 | 70 | 60 | 50 | 30 |
| Barnyardgrass | 100 | 90 | 80 | 30 | 100 | 90 | 60 | 40 | 100 | 100 | 70 | 30 | 50 | 30 | 0 | 0 | 80 | 50 | 30 | 0 |
| Blackgrass | 100 | 100 | 30 | 0 | 95 | 95 | 60 | 50 | 100 | 90 | 90 | 60 | 60 | 30 | 0 | 0 | 90 | 80 | 70 | 30 |
| Chickweed | 100 | 90 | 70 | 40 | 80 | 30 | 0 | 0 | 80 | 70 | 20 | 0 | 30 | 0 | 0 | 0 | 50 | 30 | 0 | 0 |
| Cocklebur | 100 | 90 | 70 | 0 | 80 | 30 | 0 | 0 | 70 | 40 | 20 | 0 | 60 | 30 | 0 | 0 | 50 | 40 | 30 | 0 |
| Corn | 100 | 100 | 90 | 70 | 100 | 100 | 80 | 60 | 100 | 100 | 60 | 50 | 30 | 0 | 0 | 0 | 0 | 0 | 0 | 0 |
| Cotton | 80 | 70 | 20 | 10 | 90 | 90 | 80 | 50 | 90 | 90 | 80 | 70 | 30 | 0 | 0 | 0 | 50 | 30 | 0 | 0 |
| Crabgrass | 90 | 20 | 0 | 0 | 70 | 30 | 20 | 0 | 60 | 40 | 20 | 0 | 0 | 0 | 0 | 0 | 40 | 30 | 20 | 0 |
| Downy brome | 100 | 100 | 100 | 60 | 95 | 95 | 90 | 40 | 95 | 95 | 70 | 50 | 60 | 30 | 0 | 0 | 70 | 50 | 30 | 0 |
| Giant foxtail | 70 | 40 | 0 | 0 | 100 | 40 | 20 | 0 | 90 | 70 | 0 | 0 | 0 | 0 | 0 | 0 | 50 | 30 | 0 | 0 |
| Green foxtail | 40 | 10 | 0 | 0 | 90 | 60 | 40 | 20 | 50 | 40 | 0 | 0 | 0 | 0 | 0 | 0 | 40 | 20 | 0 | 0 |
| Jimsonweed | 100 | 100 | 90 | 70 | 100 | 90 | 70 | 50 | 100 | 90 | 90 | 80 | 70 | 50 | 30 | 0 | 50 | 40 | 30 | 20 |
| Johnsongrass | — | 100 | 80 | 40 | 100 | 90 | 60 | 40 | 100 | 90 | 40 | 30 | 60 | 30 | 0 | 0 | 70 | 50 | 40 | 30 |
| Lambsquarters | 100 | 80 | 30 | — | 50 | 30 | 0 | 0 | 90 | 0 | 0 | 0 | 70 | 60 | 50 | 40 | 90 | 70 | 50 | 0 |
| Morningglory | 100 | 90 | 80 | 50 | 100 | 100 | 100 | 0 | 100 | 100 | 90 | 80 | 90 | 50 | 30 | 0 | 80 | 50 | 30 | 0 |
| Nutsedge | 100 | 100 | 90 | 40 | 100 | 100 | 100 | 0 | 100 | 100 | 100 | 100 | 50 | 30 | 0 | 0 | 90 | 30 | 0 | 0 |
| Rape | 100 | 100 | 100 | 80 | 90 | 90 | 30 | 0 | 100 | 100 | 80 | 50 | 90 | 70 | 50 | 30 | 100 | 100 | 100 | 100 |
| Rice | 100 | 100 | 80 | 50 | 100 | 100 | 100 | 90 | 100 | 100 | 100 | 70 | 30 | 0 | 0 | 0 | 60 | 40 | 30 | 0 |
| Sicklepod | 100 | 100 | 90 | 80 | 100 | 90 | 90 | 0 | 100 | 100 | 90 | 70 | 0 | 0 | 0 | 0 | 30 | 0 | 0 | 0 |
| Soybean | 90 | 90 | 80 | 80 | 90 | 90 | 90 | 70 | 90 | 90 | 80 | 50 | 90 | 60 | 30 | 0 | 90 | 70 | 60 | 50 |
| Sugar beet | 20 | 0 | 0 | 0 | 70 | 0 | 0 | 0 | 40 | 0 | 0 | 0 | 0 | 0 | 0 | 0 | 30 | 0 | 0 | 0 |
| Teaweed | 90 | 80 | 70 | 50 | 80 | 30 | 0 | 0 | 70 | 50 | 20 | 0 | 40 | 30 | 20 | 0 | 50 | 30 | 0 | 0 |
| Velvetleaf | 100 | 100 | 80 | 80 | 90 | 90 | 70 | 50 | 100 | 100 | 100 | 90 | 60 | 30 | 0 | 0 | 90 | 70 | 50 | 40 |
| Wheat | 90 | 70 | 70 | 40 | 90 | 90 | 80 | 40 | 90 | 90 | 60 | 30 | 40 | 0 | 0 | 0 | 40 | 30 | 0 | 0 |
| Wild buckwheat | 100 | 80 | 70 | 20 | 80 | 80 | 20 | 0 | 100 | 50 | 0 | 0 | 0 | 0 | 0 | 0 | 60 | 0 | 0 | 0 |
| Wild oat | 100 | 60 | 60 | 30 | 95 | 60 | 40 | 0 | 95 | 80 | 40 | 20 | 30 | 0 | 0 | 0 | 70 | 60 | 30 | 0 |

| | 6 | | | | 7 | | | | 9 | | | |
|---|---|---|---|---|---|---|---|---|---|---|---|---|
| RATE (g/ha) | 250 | 62 | 16 | 4 | 250 | 62 | 16 | 4 | 250 | 62 | 16 | 4 |
| Barley | 70 | 60 | 50 | 40 | 90 | 70 | 60 | 50 | 80 | 60 | 60 | 60 |
| Barnyardgrass | 50 | 40 | 30 | 20 | 80 | 70 | 60 | 30 | 80 | 75 | 70 | 50 |
| Blackgrass | 100 | 100 | 90 | 70 | 90 | 80 | 70 | 30 | 90 | 80 | 70 | 40 |
| Chickweed | 70 | 60 | 50 | 30 | 90 | 80 | 50 | 30 | 80 | 70 | 50 | 30 |
| Cocklebur | 75 | 70 | 60 | 50 | 100 | 90 | 80 | 70 | 90 | 80 | 60 | 30 |
| Corn | 70 | 60 | 50 | 40 | 75 | 70 | 60 | 50 | 90 | 80 | 70 | 50 |
| Cotton | 70 | 60 | 40 | 30 | 80 | 70 | 60 | 50 | 70 | 60 | 50 | 40 |
| Crabgrass | 60 | 50 | 40 | 30 | 50 | 30 | 0 | 0 | 40 | 30 | 0 | 0 |
| Downy brome | 80 | 70 | 60 | 40 | 90 | 70 | 60 | 50 | 90 | 80 | 70 | 60 |
| Giant foxtail | 30 | 30 | 20 | 20 | 60 | 30 | 0 | 0 | 60 | 50 | 30 | 0 |
| Green foxtail | 50 | 40 | 30 | 20 | 60 | 30 | 0 | 0 | 80 | 70 | 50 | 40 |
| Jimsonweed | 90 | 85 | 80 | 70 | 100 | 100 | 90 | 80 | 100 | 100 | 90 | 70 |
| Johnsongrass | 90 | 80 | 70 | 60 | 90 | 80 | 70 | 50 | 90 | 80 | 70 | 60 |
| Lambsquarters | 90 | 80 | 70 | 60 | 90 | 80 | 70 | 60 | 40 | 30 | 0 | 0 |
| Morningglory | 85 | 80 | 75 | 70 | 100 | 100 | 100 | 90 | 100 | 100 | 90 | 80 |
| Nutsedge | 70 | 60 | 50 | 30 | 90 | 80 | 70 | 60 | 100 | 90 | 60 | 30 |
| Rape | 100 | 100 | 100 | 70 | 100 | 100 | 90 | 70 | 100 | 100 | 100 | 90 |
| Rice | 80 | 70 | 60 | 50 | 80 | 70 | 60 | 50 | 70 | 70 | 70 | 70 |
| Sicklepod | 80 | 70 | 60 | 50 | 95 | 90 | 80 | 70 | 100 | 80 | 70 | 60 |
| Soybean | 90 | 85 | 80 | 70 | 100 | 90 | 80 | 70 | 100 | 100 | 90 | 60 |
| Sugar beet | 20 | 0 | 0 | 0 | 20 | 0 | 0 | 0 | 0 | 0 | 0 | 0 |
| Teaweed | 70 | 60 | 50 | 30 | 70 | 60 | 50 | 40 | 80 | 70 | 60 | 50 |
| Velvetleaf | 95 | 90 | 80 | 70 | 95 | 90 | 80 | 70 | 100 | 100 | 90 | 70 |
| Wheat | 60 | 50 | 30 | 0 | 100 | 70 | 50 | 30 | 60 | 50 | 50 | 50 |
| Wild buckwheat | 100 | 100 | 90 | 70 | 90 | 80 | 70 | 60 | — | — | — | — |
| Wild oat | 80 | 75 | 70 | 60 | 90 | 70 | 50 | 0 | 70 | 60 | 50 | 40 |

PREEMERGENCE

| | Cmpd 1 | | | 2 | | | | 3 | | | | 4 | | | 5 | | | |
|---|---|---|---|---|---|---|---|---|---|---|---|---|---|---|---|---|---|---|
| RATE (g/ha) | 250 | 62 | 16 | 250 | 62 | 16 | 4 | 250 | 62 | 16 | 4 | 250 | 62 | 16 | 250 | 62 | 16 | 4 |
| Barley | 90 | 80 | 40 | 70 | 60 | 20 | 0 | 80 | 70 | 40 | 0 | 30 | 0 | 0 | 70 | 50 | 0 | 0 |
| Barnyardgrass | 100 | 100 | 60 | 100 | 70 | 20 | 0 | 70 | 20 | 0 | 0 | 90 | 60 | 30 | 90 | 70 | 50 | 0 |
| Blackgrass | 80 | — | 40 | 50 | 30 | 0 | 0 | 70 | 70 | 40 | 30 | 80 | 50 | 0 | 90 | 60 | 30 | 0 |
| Chickweed | 90 | 80 | 50 | 30 | 20 | 0 | 0 | 70 | 70 | 30 | 30 | 60 | 30 | 0 | 70 | 50 | 30 | 0 |
| Cocklebur | 90 | 80 | 30 | 90 | 30 | 0 | 0 | 60 | 40 | 30 | 0 | 80 | 30 | 0 | 70 | 50 | 30 | 0 |
| Corn | 100 | 90 | 70 | 100 | 70 | 70 | 20 | 100 | 100 | 30 | 0 | 60 | 20 | 0 | 80 | 60 | 0 | 0 |
| Cotton | 30 | 20 | 0 | 80 | 20 | 0 | 0 | 0 | 0 | 0 | 0 | 0 | 0 | 0 | 0 | 0 | 0 | 0 |
| Crabgrass | 50 | 50 | 30 | 50 | 30 | 30 | 0 | 90 | 80 | 70 | 0 | 80 | 50 | 30 | 100 | 80 | 30 | 0 |
| Downy brome | 90 | 80 | 40 | 100 | 70 | 20 | 0 | 100 | 40 | 20 | 0 | 70 | 30 | 0 | 70 | 50 | 0 | 0 |
| Giant foxtail | 90 | 70 | 40 | 90 | 50 | 20 | 0 | 70 | 30 | 0 | 0 | 60 | 30 | 0 | 90 | 80 | 50 | 30 |
| Green foxtail | 100 | 80 | 60 | 90 | 70 | 20 | 0 | 70 | 30 | 0 | 0 | 80 | 30 | 0 | 90 | 70 | 50 | 0 |
| Jimsonweed | 100 | 50 | 30 | 90 | 50 | 20 | 0 | 70 | 40 | 30 | 0 | 70 | 30 | 0 | 70 | 50 | 30 | 0 |
| Johnsongrass | 100 | 100 | 90 | 90 | 80 | 20 | 0 | 90 | 80 | 40 | 0 | 60 | 30 | 0 | 80 | 60 | 30 | 0 |
| Lambsquarters | 100 | 60 | 20 | 80 | 70 | 70 | 0 | 80 | 70 | 50 | 0 | 90 | 60 | 30 | 90 | 80 | 70 | 60 |
| Morningglory | 100 | 80 | 40 | 100 | 60 | 20 | 0 | 70 | 70 | 0 | 0 | 60 | 30 | 0 | 90 | 60 | 50 | 30 |
| Nutsedge | 100 | 70 | 20 | 30 | 20 | 0 | 0 | 40 | — | 20 | 0 | 50 | 30 | 0 | 90 | 70 | 0 | 0 |

TABLE B-continued

| | | | | | | | | | | | | | | | | | | | |
|---|---|---|---|---|---|---|---|---|---|---|---|---|---|---|---|---|---|---|---|
| Rape | 100 | 90 | 50 | 100 | 50 | 0 | 0 | 100 | 70 | 20 | 0 | 70 | 50 | 30 | 90 | 70 | 30 | 0 |
| Rice | 100 | 80 | 30 | 70 | 30 | 20 | 0 | 90 | 60 | 20 | 0 | 40 | 0 | 0 | 40 | 20 | 0 | 0 |
| Sicklepod | 100 | 60 | 50 | 30 | 20 | 0 | 0 | 40 | 20 | 0 | 0 | 30 | 0 | 0 | 70 | 50 | 30 | 0 |
| Soybean | 90 | 50 | 30 | 100 | 20 | 0 | 0 | 30 | 0 | 0 | 0 | 20 | 0 | 0 | 60 | 30 | 0 | 0 |
| Sugar beet | 70 | 30 | 0 | 70 | 20 | 0 | 0 | 40 | 20 | 0 | 0 | 30 | 0 | 0 | 30 | 0 | 0 | 0 |
| Teaweed | 80 | 60 | 30 | 50 | 40 | 20 | 0 | 100 | 100 | 30 | 0 | 70 | 50 | 30 | 70 | 60 | 50 | 30 |
| Velvetleaf | 90 | 80 | 70 | 80 | 20 | — | — | 80 | 80 | 0 | 0 | 90 | 50 | 0 | 70 | 30 | 0 | 0 |
| Wheat | 90 | 70 | 40 | 80 | 50 | 20 | 0 | 70 | 40 | 20 | 0 | 40 | 0 | 0 | 60 | 30 | 0 | 0 |
| Wild buckwheat | 90 | 60 | 20 | 90 | 80 | 80 | 20 | 90 | 80 | 80 | 80 | 0 | 0 | 0 | 0 | 0 | 0 | 0 |
| Wild oat | 60 | 60 | 20 | 60 | 20 | 0 | 0 | 80 | 50 | 30 | 0 | 40 | 0 | 0 | 40 | 30 | 0 | 0 |

| | | 6 | | | | 7 | | | | 9 | | |
|---|---|---|---|---|---|---|---|---|---|---|---|---|
| RATE (g/ha) | | 250 | 62 | 16 | 4 | 250 | 62 | 16 | 4 | 250 | 62 | 16 | 4 |
| Barley | | 90 | 80 | 70 | 30 | 70 | 60 | 30 | 0 | 90 | 70 | 50 | 30 |
| Barnyardgrass | | 100 | 90 | 50 | 30 | 90 | 80 | 50 | 30 | 100 | 90 | 80 | 30 |
| Blackgrass | | 100 | 100 | 90 | 70 | 90 | 80 | 70 | 30 | 100 | 100 | 90 | 50 |
| Chickweed | | 100 | 100 | 90 | 70 | 100 | 100 | 90 | 70 | 70 | 50 | 30 | 0 |
| Cocklebur | | 90 | 70 | 50 | 30 | 70 | 60 | 50 | 0 | 90 | 70 | 40 | 0 |
| Corn | | 100 | 80 | 70 | 20 | 90 | 60 | 30 | 0 | 90 | 80 | 70 | 30 |
| Cotton | | 60 | 0 | 0 | 0 | 30 | 20 | 0 | 0 | 50 | 40 | 0 | 0 |
| Crabgrass | | 80 | 50 | 30 | 0 | 80 | 50 | 30 | 0 | 80 | 30 | 0 | 0 |
| Downy brome | | 100 | 100 | 80 | 50 | 100 | 80 | 50 | 0 | 100 | 90 | 70 | 60 |
| Giant foxtail | | 80 | 50 | 30 | 0 | 60 | 30 | 0 | 0 | 90 | 70 | 30 | 0 |
| Green foxtail | | 80 | 50 | 30 | 0 | 70 | 30 | 0 | 0 | 90 | 70 | 50 | 30 |
| Jimsonweed | | 90 | 80 | 70 | 60 | 90 | 70 | 50 | 30 | 90 | 70 | 50 | 30 |
| Johnsongrass | | 90 | 80 | 70 | 50 | 80 | 70 | 30 | 0 | 95 | 90 | 80 | 50 |
| Lambsquarters | | 100 | 100 | 90 | 80 | 100 | 100 | 50 | 30 | 90 | 70 | 50 | 0 |
| Morningglory | | 90 | 80 | 70 | 60 | 90 | 70 | 50 | 30 | 90 | 80 | 70 | 50 |
| Nutsedge | | 90 | 60 | 30 | 0 | 70 | 50 | 30 | 0 | 100 | 50 | 0 | 0 |
| Rape | | 100 | 100 | 90 | 70 | 100 | 100 | 70 | 30 | 100 | 100 | 90 | 70 |
| Rice | | 100 | 100 | 80 | 30 | 80 | 60 | 30 | 0 | 100 | 80 | 50 | 30 |
| Sicklepod | | 90 | 70 | 60 | 50 | 70 | 60 | 0 | 0 | 80 | 70 | 40 | 0 |
| Soybean | | 80 | 40 | 0 | 0 | 70 | 30 | 0 | 0 | 70 | 60 | 40 | 0 |
| Sugar beet | | 90 | 70 | 60 | 50 | 50 | 40 | 30 | 0 | 50 | 30 | 0 | 0 |
| Teaweed | | 90 | 80 | — | 50 | 90 | 70 | 40 | 30 | 80 | 70 | 50 | 0 |
| Velvetleaf | | 90 | 70 | 50 | 30 | 80 | 70 | 50 | 0 | 100 | 100 | 95 | 90 |
| Wheat | | 90 | 60 | 30 | 0 | 80 | 30 | 0 | 0 | 100 | 70 | 50 | 30 |
| Wild buckwheat | | 95 | 90 | 85 | 80 | 100 | 70 | 60 | 50 | — | — | — | — |
| Wild oat | | 80 | 50 | 30 | 0 | 70 | 50 | 30 | 0 | 70 | 60 | 50 | 30 |

TEST C

Seeds selected from crop and weed species consisting of annual bluegrass (*Poa annua*), barley (*Hordeum vulgare*), black nightshade (*Solanum nigrum*), blackgrass (*Alopecurues myosuroides*), catchweed bedstraw (*Galium aparine*), chickweed (*Stellaria media*), green foxtail (*Setaria viridis*), Italian ryegrass (*Lolium multiflorum*), knotweed (polygonum aviculare), kochia (*Kochia scoparia*), lambsquarters (*Chenopodium album*), pigweed (*Amaranthus retroflexus*), rape (*Brassica napus*), scentless chamomile (*Matricaria inodora*), smartweed (*Polygonum persicaria*), speedwell (*Veronica persica*), sugar beet (*Beta vulgaris*), viola (*Viola arvensis*), wheat (*Triticum aestivum*), wild buckwheat (*Polygonum convolvulus*), wild mustard (*Brassica* spp.), wild oat (*Avena fatua*) and wild radish (*Raphanus raphanistrum*) were planted and treated preemergence with test chemicals dissolved in a non-phytotoxic solvent. Selected species from this list of crops and weeds were also treated with postemergence applications of test chemicals. Plants ranged in height from two to twenty cm (two to three leaf stage) for postemergence treatments. Treated plants and controls were maintained in a greenhouse for approximately 24 days, after which all species were compared to controls and visually evaluated. The ratings, summarized in Table C, are based on a scale of 0 to 100 where 0 is no effect and 100 is complete control. A dash (—) response means no test.

TABLE C

| | POSTEMERGENCE | | | | | | | | | | | | | | | | |
|---|---|---|---|---|---|---|---|---|---|---|---|---|---|---|---|---|---|
| | Cmpd 1 | | | | 2 | | | | | 3 | | | | | 4 | | |
| RATE (g/ha) | 64 | 32 | 16 | 8 | 250 | 125 | 64 | 32 | 16 | 250 | 125 | 64 | 32 | 16 | 64 | 32 | 16 | 8 |
| Annual bluegrass | 70 | 70 | 30 | 0 | 100 | 80 | 80 | 40 | 0 | 100 | 60 | 60 | 20 | 20 | | | | |
| Barley | 85 | 70 | 75 | 50 | 100 | 100 | 80 | 80 | 70 | 80 | 80 | 80 | 70 | 50 | | | | |
| Black nightshade | 100 | 100 | 100 | 75 | | | | | | | | | | | | | | |
| Blackgrass | 100 | 100 | 80 | 50 | 100 | 100 | 100 | 100 | 0 | 100 | 100 | 80 | 30 | 20 | 50 | 50 | 30 | 0 |
| Catchweed bedstraw | 100 | 90 | 75 | 0 | | | | | | | | | | | 20 | 20 | 0 | 0 |
| Chickweed | 85 | 60 | 40 | 20 | 20 | 20 | 0 | 0 | 0 | 90 | 50 | 20 | 20 | 0 | 30 | 20 | 0 | 0 |
| Green foxtail | 50 | 0 | 0 | 0 | 80 | 80 | 40 | 40 | 40 | 90 | 80 | 40 | 40 | 20 | | | | |
| Italian ryegrass | 100 | 50 | 50 | 0 | | | | | | | | | | | | | | |
| Knotweed | | | | | | | | | | | | | | | — | 20 | 0 | 0 |
| Kochia | 90 | 100 | 50 | 20 | | | | | | | | | | | | | | |
| Lambsquarters | 0 | 0 | 0 | 0 | 100 | 60 | 60 | 60 | 30 | 100 | 30 | 0 | 0 | 0 | 20 | 0 | — | — |
| Pigweed | 40 | 40 | 30 | 0 | 100 | 100 | 80 | 60 | 60 | 100 | 100 | 40 | 20 | | | | | |
| Rape | 90 | 90 | 75 | 60 | | | | | | | | | | | | | | |
| Scentless chamomile | 100 | 100 | 90 | 30 | | | | | | | | | | | 70 | 50 | 50 | 50 |
| Smartweed | | | | | 100 | 100 | 90 | 90 | 90 | 100 | 100 | 100 | 90 | 90 | | | | |
| Speedwell | 100 | 90 | 50 | 30 | | | | | | | | | | | 80 | 50 | 30 | 30 |
| Sugar beet | 0 | 0 | 0 | 0 | 50 | 30 | 0 | 0 | 0 | 20 | 0 | 0 | 0 | 0 | 20 | 0 | 0 | 0 |

TABLE C-continued

| | | | | | | | | | | | | | | | | | | | |
|---|---|---|---|---|---|---|---|---|---|---|---|---|---|---|---|---|---|---|---|
| Viola | | | | | | | | | | | | | | | 0 | 0 | 0 | 0 |
| Wheat | 75 | 75 | 50 | 50 | | | | | | | | | | | 40 | 40 | 30 | 30 |
| Wild buckwheat | 100 | 80 | 60 | 40 | 100 | 100 | 100 | 100 | 80 | 100 | 95 | 100 | 90 | 90 | 40 | 30 | 20 | 0 |
| Wild mustard | 100 | 100 | 100 | 100 | 100 | 100 | 100 | 100 | 100 | 100 | 100 | 100 | 100 | 100 | | | | |
| Wild oat | 70 | 70 | 50 | 30 | 90 | 80 | 70 | 60 | 50 | 50 | 50 | 0 | 0 | 0 | 50 | 40 | 40 | 40 |
| Wild radish | 100 | 100 | 100 | 100 | | | | | | | | | | | | | | |

POSTEMERGENCE

| | 5 | | | | 6 | | | | 7 | | | | 8 | 9 | | | | |
|---|---|---|---|---|---|---|---|---|---|---|---|---|---|---|---|---|---|---|
| RATE (g/ha) | 125 | 64 | 32 | 16 | 125 | 64 | 32 | 16 | 125 | 64 | 32 | 16 | 125 | 125 | 64 | 32 | 16 | 8 |
| Blackgrass | 50 | 50 | 50 | 20 | 100 | 80 | 80 | 50 | 90 | 90 | 50 | 50 | 50 | 100 | 100 | 100 | 100 | 100 |
| Catchweed bedstraw | 70 | 70 | 70 | 30 | 90 | 60 | 60 | 30 | 80 | 80 | 80 | 50 | 60 | 100 | 90 | 90 | 90 | 70 |
| Chickweed | 0 | 0 | 0 | 0 | 0 | 0 | 0 | 0 | 80 | 50 | 20 | 0 | 30 | 80 | 30 | 30 | 0 | 0 |
| Knotweed | — | 50 | 50 | 0 | — | 50 | — | 50 | | | | | | 90 | 90 | 90 | 70 | 70 |
| Lambsquarters | — | — | — | 0 | | | | | | | | | 0 | | | | | |
| Scentless chamomile | 50 | 30 | 20 | 20 | 100 | 80 | 80 | 80 | 100 | 100 | 100 | 80 | 85 | 100 | 100 | 100 | 70 | 50 |
| Speedwell | 80 | 60 | 50 | 50 | 100 | 80 | 80 | 30 | 100 | 100 | 50 | 50 | 80 | 100 | 100 | 100 | 80 | 80 |
| Sugar beet | 15 | 0 | 0 | 0 | 20 | 0 | 0 | 0 | 0 | 0 | 0 | 0 | 30 | 15 | 0 | 0 | 0 | 0 |
| Viola | 30 | 30 | 0 | 0 | 70 | 70 | 70 | 20 | 100 | 100 | 50 | 30 | 60 | 100 | 100 | 80 | 50 | 30 |
| Wheat | 50 | 30 | 30 | 30 | 80 | 80 | 70 | 50 | 80 | 80 | 70 | 50 | 70 | 100 | 60 | 50 | 50 | 50 |
| Wild buckwheat | 50 | 50 | 20 | 20 | 100 | 100 | 80 | 70 | 100 | 90 | 80 | 80 | 70 | 100 | 90 | 80 | 70 | 60 |
| Wild oat | 70 | 50 | 50 | 50 | 100 | 70 | 70 | 70 | 80 | 80 | 50 | 50 | | 100 | 90 | 80 | 80 | 80 |

PREEMERGENCE

| | Cmpd 1 | | 2 | | 3 | | 4 | 5 | | 6 | | | 7 | | 8 | 9 | | |
|---|---|---|---|---|---|---|---|---|---|---|---|---|---|---|---|---|---|---|---|
| RATE (g/ha) | 64 | 32 | 64 | 32 | 64 | 32 | 64 | 125 | 64 | 125 | 64 | 32 | 125 | 64 | 32 | 125 | 125 | 64 | 32 |
| Annual bluegrass | 75 | 30 | 20 | 0 | 20 | 0 | | | | | | | | | | | | | |
| Barley | 70 | 40 | 70 | 30 | 50 | 30 | | | | | | | | | | | | | |
| Black nightshade | 30 | 0 | | | | | | | | | | | | | | | | | |
| Blackgrass | 100 | 100 | 70 | 40 | 30 | 30 | 50 | 90 | 70 | 100 | 80 | 80 | 80 | 80 | 40 | 50 | 100 | 100 | 90 |
| Catchweed bedstraw | 100 | 0 | | | | | | 90 | 80 | 90 | 80 | 80 | 90 | 90 | 90 | 0 | 100 | 100 | 90 |
| Chickweed | 60 | 0 | 0 | 0 | 0 | 0 | 30 | 80 | 50 | 80 | 80 | 70 | 80 | 70 | 70 | 30 | 100 | 100 | 100 |
| Green foxtail | 0 | 0 | 60 | 20 | 20 | 0 | | | | | | | | | | | | | |
| Italian ryegrass | 60 | 50 | | | | | | | | | | | | | | | | | |
| Knotweed | | | | | | | | | | | 30 | | 0 | 0 | 0 | | 100 | 100 | |
| Kochia | 0 | 0 | | | | | | | | | | | | | | | | | |
| Lambsquarters | 0 | 0 | 0 | 0 | 50 | 0 | | | | | | | | | | | | | |
| Pigweed | 0 | 0 | 40 | 20 | 0 | 0 | | | | | | | | | | | | | |
| Rape | 75 | 20 | | | | | | | | | | | | | | | | | |
| Scentless chamomile | 90 | 90 | | | | | 80 | 90 | 90 | 90 | 80 | 80 | 90 | 90 | 50 | 0 | 100 | 100 | 100 |
| Smartweed | | | 90 | 80 | 50 | 50 | | | | | | | | | | | | | |
| Speedwell | 60 | — | | | | | 30 | 100 | 80 | 100 | 100 | 100 | 100 | 80 | 50 | 50 | 100 | 100 | 100 |
| Sugar beet | 0 | 0 | 0 | 0 | 30 | 0 | 0 | 80 | 30 | 90 | 90 | 80 | 30 | 30 | 10 | 0 | 100 | 80 | 80 |
| Wheat | 40 | 20 | | | | | 20 | 70 | 30 | 70 | 60 | 40 | 0 | 0 | 0 | 0 | 90 | 90 | 70 |
| Wild buckwheat | 20 | 0 | 20 | 0 | 0 | 0 | 0 | 30 | 30 | 90 | 90 | 80 | 85 | 70 | 70 | 30 | 100 | 100 | 100 |
| Wild mustard | 75 | 20 | 100 | 50 | 80 | 0 | | | | | | | | | | | | | |
| Wild oat | 70 | 50 | 70 | 0 | 30 | 0 | 30 | 70 | 70 | 80 | 80 | 60 | 80 | 50 | 30 | 40 | 90 | 80 | 70 |
| Wild radish | 30 | 0 | | | | | | | | | | | | | | | | | |

What is claimed is:

1. A compound of the formula

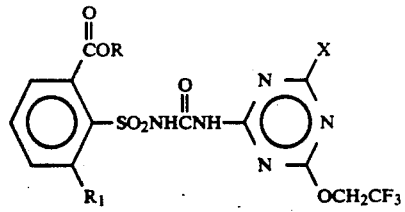

I wherein
R is $C_1$–$C_4$ alkyl, $CH_2CH=CH_2$, $CH_2C\{CH$, cyclopropylmethyl or $CH_2CH_2R_2$;
$R_1$ is $C_1$–$C_2$ alkyl, $C_1$–$C_2$ haloalkyl, $CH_2CN$, $CH_2CH_3$, $C_1$–$C_3$ alkoxy, $C_1$–$C_3$ alkylthio, phenylthio or $NR_3R_4$;
$R_2$ is $C_1$–$C_2$ alkoxy, $C_1$–$C_2$ alkylthio, CN or halogen;
$R_3$ and $R_4$ are independently H or $CH_3$; and
X is $NHCH_3$, $N(CH_3)_2$ or $N(CH_3)OCH_3$; provided that when $R_1$ is $OCH_2CH_3$ or $CH_2OCH_3$, then R is other than $CH_3$;
and their agriculturally suitable salts.

2. The compounds of claim 1 wherein
R is $C_1$–$C_4$ alkyl;
$R_1$ is $C_1$–$C_2$ alkyl; and
X is $NHCH_3$ or $N(CH_3)_2$.

3. The compounds of claim 1 wherein
R is $C_1$–$C_4$ alkyl;
$R_1$ is $C_1$–$C_2$ haloalkyl; and
X is $NHCH_3$ or $N(CH_3)_2$.

4. The compounds of claim 2 wherein
R is $C_1$–$C_3$ alkyl; and
X is $NHCH_3)_2$.

5. The compounds of claim 2 wherein
R is $C_1$–$C_3$ alkyl; and
X is $N(CH_3)_2$.

6. A compound of claim 1 which is
ethyl 2-[[[[[4-(dimethylamino)-6-(2,2,2-trifluoroethoxy)-1,3,5-triazin-2-yl]amino]carbonyl]amino]-sulfonyl]-3-methylbenzoate.

7. A compound of claim 1 which is
methyl 2-[[[[[4-(dimethylamino)-6-(2,2,2-trifluoroethoxy)-1,3,5-triazin-2-yl]amino]carbonyl]amino]-sulfonyl]-3-methylbenzoate.

8. A composition suitable for controlling the growth of undesired vegetation which comprises an effective amount of a compound of claim 1 and at least one of the following: surfactant, solid diluent or liquid diluent.

9. A composition suitable for controlling the growth of undesired vegetation which comprises an effective amount of a compound of claim 2 and at least one of the following: surfactant, solid diluent or liquid diluent.

10. A composition suitable for controlling the growth of undesired vegetation which comprises an effective amount of a compound of claim 3 and at least one of the following: surfactant, solid diluent or liquid diluent.

11. A composition suitable for controlling the growth of undesired vegetation which comprises an effective amount of a compound of claim 4 and at least one of the following: surfactant, solid diluent or liquid diluent.

12. A composition suitable for controlling the growth of undesired vegetation which comprises an effective amount of a compound of claim 5 and at least one of the following: surfactant, solid diluent or liquid diluent.

13. A composition suitable for controlling the growth of undesired vegetation which comprises an effective amount of a compound of claim 6 and at least one of the following: surfactant, solid diluent or liquid diluent.

14. A composition suitable for controlling the growth of undesired vegetation which comprises an effective amount of a compound of claim 7 and at least one of the following: surfactant, solid diluent or liquid diluent.

15. A method for the control of undesired vegetation which comprises applying to the locus to be protected an effective amount of a compound of claim 1.

16. A method for the control of undesired vegetation which comprises applying to the locus to be protected an effective amount of a compound of claim 2.

17. A method for the control of undesired vegetation which comprises applying to the locus to be protected an effective amount of a compound of claim 3.

18. A method for the control of undesired vegetation which comprises applying to the locus to be protected an effective amount of a compound of claim 4.

19. A method for the control of undesired vegetation which comprises applying to the locus to be protected an effective amount of a compound of claim 5.

20. A method for the control of undesired vegetation which comprises applying to the locus to be protected an effective amount of a compound of claim 6.

21. A method for the control of undesired vegetation which comprises applying to the locus to be protected an effective amount of a compound of claim 7.

22. The method of claim 20 wherein the locus to be protected is a sugar beet crop.

23. The method of claim 21 wherein the locus to be protected is a sugar beet crop.

* * * * *

UNITED STATES PATENT AND TRADEMARK OFFICE
CERTIFICATE OF CORRECTION

PATENT NO. : 5,090,993

DATED : February 25, 1992

INVENTOR(S) : Marcus P. Moon

It is certified that error appears in the above-identified patent and that said Letters Patent is hereby corrected as shown below:

Column 1, lines 26, 54, 55, and 59; column 2, lines 17 and 23, "inter alia", at each occurrence should read --<u>inter alia</u>--.

Column 2, line 21, "bonyl, $-NR_{45}R_{46}$, $-SO_3H$ or $-SO_2NR_{47}R_{48}$"; should read --bonyl, $-NR_{45}R_{46}$, $-SO_3H$ or $-SO_2NR_{47}R_{48}$--.

Column 2, line 54, "X is $NHCH_3$, $N(CH_3)_2$ or $N(CH_3)OCH_3$; provided" should read --X is $NHCH_3$, $N(CH_3)_2$ or $N(CH_3)OCH_3$; provided Column 3, line 35, "thyoxy)-1,3,5-triazin-2-yl]amino]carbonyl]amino]sul-" should read --thoxy)-1,3,5-triazin-2-yl]amino]carbonyl]amino]sul- --.

Column 7, line 67, "(Phenylmethylthio)-benzoate (24 g), dichloromethane should read --(phenylmethylthio)-benzoate (24 g), dichloromethane--.

Column 8, line 40 "butyllithium (46 mL) at 50° C. and allowed to warm to" should read --butyllithium (46 mL) at -50° C. and allowed to warm to--.

Column 8, line 53, "MHz NMR (CDC13): δ0.29 (s, 6H, $SiCH_3$); 0.96 (s," should read --90MHz NMR (CDC13): δ0.29 (s, 6H, $SiCH_3$); 0.96 (s,--.

UNITED STATES PATENT AND TRADEMARK OFFICE
CERTIFICATE OF CORRECTION

PATENT NO. : 5,090,993
DATED : February 25, 1992
INVENTOR(S) : Marcus P. Moon It is certified that error appears in the above-identified patent and that said Letters Patent is hereby corrected as shown below:

Column 8, line 66, "and O-phenyl-N-[4-dimethylamino-6-(2,2,2-trifluoroe-" should read --and O-phenyl-N-[4-dimethylamino-6-(2,2,2-trifluoroe- --.

Column 9, line 6, "200 MHz NMR (CDC13): δ 6 1.38 (t, 3H, CH3); 2.89" should read --200 MHz NMR (CDC13): δ1.38 (t, 3H, CH3); 2.89--.

Column 9, line 19, "thyl)silylamino)-3-methylbenzoate (0.68 g) and -phenyl-" should read --thyl)silylamino)-3-methylbenzoate (0.68 g) and O-phenyl- --.

Column 9, line 32, "300 MHz NMR (DMSO): δ6 3.04 (s, 3H, CH3); 3.46" should read --300 MHz NMR (DMSO): δ3.04 (s, 3H, CH3); 3.46--.

Column 9, Table 1, lines 40-47,
"TABLE I

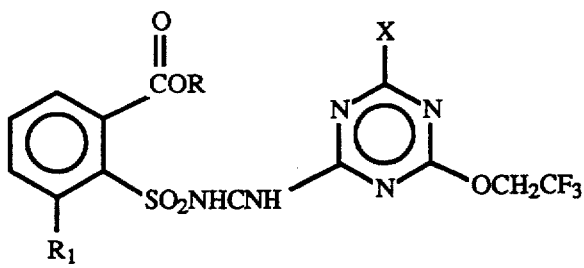

"

UNITED STATES PATENT AND TRADEMARK OFFICE
CERTIFICATE OF CORRECTION

PATENT NO. : 5,090,993  Page 3 of 7
DATED : February 25, 1992
INVENTOR(S) : Marcus P. Moon It is certified that error appears in the above-identified patent and that said Letters Patent is hereby corrected as shown below:

should read --

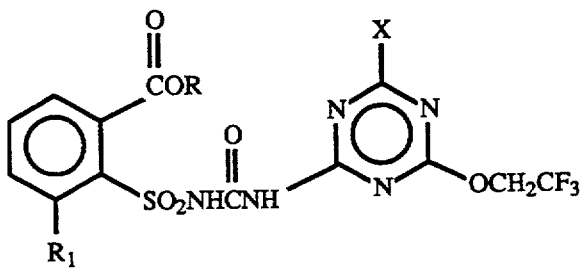

--.

Column 10, lines 1-8,

"

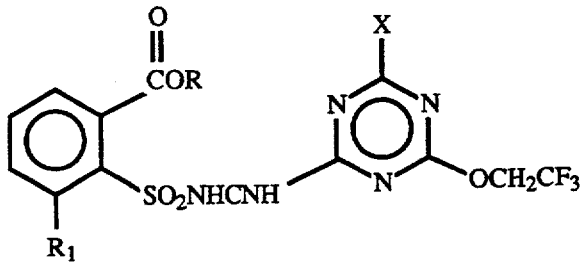

"

UNITED STATES PATENT AND TRADEMARK OFFICE
CERTIFICATE OF CORRECTION

PATENT NO. : 5,090,993

DATED : February 25, 1992

INVENTOR(S) : Marcus P. Moon

It is certified that error appears in the above-identified patent and that said Letters Patent is hereby corrected as shown below:

should read --

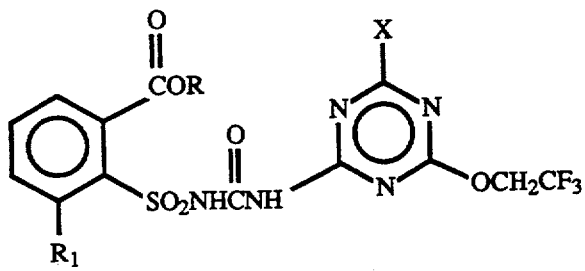

--.

Column 11, lines 1-8,

"

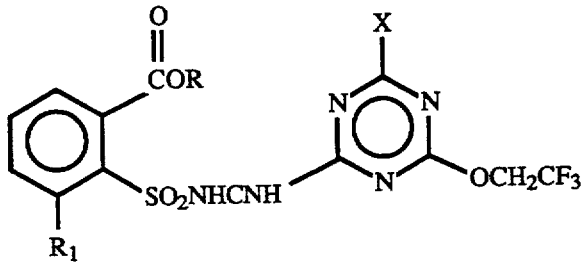

" .

UNITED STATES PATENT AND TRADEMARK OFFICE
CERTIFICATE OF CORRECTION

PATENT NO. : 5,090,993
DATED : February 25, 1992
INVENTOR(S) : Marcus P. Moon It is certified that error appears in the above-identified patent and that said Letters Patent is hereby corrected as shown below:

should read --

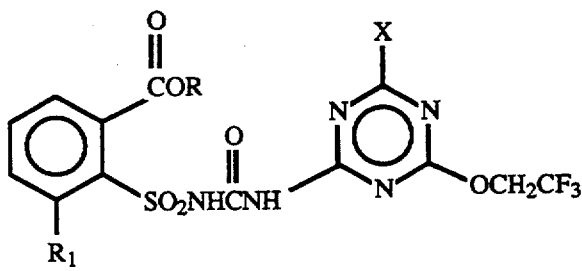

--.

Column 14, line 29, "The ingredients are blended and milled to Pass" should read --The ingredients are blended and milled to pass--.

Column 14, line 67, "disodium phosphate        1%" should read --disodium phosphate        1.0%--.

Column 17, line 5, "sis) and blackgrass (Alopercurus mysoroides)." should read --sis) and blackgrass (Alopercurus mysoroides).--.

UNITED STATES PATENT AND TRADEMARK OFFICE
CERTIFICATE OF CORRECTION

PATENT NO. : 5,090,993

DATED : February 25, 1992

INVENTOR(S) : Marcus P Moon

It is certified that error appears in the above-identified patent and that said Letters Patent is hereby corrected as shown below:

Column 18, line 28, "*theophrasti)*, wheat *(Triticum aestivum)*, and wild oat" should read --*theophrasti)*, wheat *(Triticum aestivum)*, wild oat--.

Column 18, line 36, "Treated Plants and controls were maintained in a green-" should read --Treated plants and controls were maintained in a green--.

Column 20, line 57, "(Polygonum convolvulus), and wild oat (Avena fatua)" should read --(Polygonum convolvulus), wild oat (Avena fatua)--.

Column 25, line 57, "R is $C_1$-$C_4$ alkyl, $CH_2CH=CH_2$, $CH_2C\{CH$, cyclo-" should read --R is $C_1$-$C_4$ alkyl, $CH_2CH=CH_2$, $CH_2C\equiv CH$ cyclo- --.

Column 25, line 60, "$CH_2CH_3$, $C_1$-$C_3$ alkoxy, $C_1$-$C_3$ alkylthio, phe-" should read --$CH_2OCH_3$, $C_1$-$C_3$ alkoxy, $C_1$-$C_3$ alkylthio, phe- --.

Column 25, line 65 and 66, "that when $R_1$ is $OCH_2CH_3$ or $CH_2OCH_3$, then R is other than $CH_3$;" should read --that when $R_1$ is $OCH_2CH_3$ or $CH_2OCH_3$, then R is other than $CH_3$;--.

Column 26, line 53, "X is $NHCH_3)_2$." should read --X is $NH(CH_3)_2$.--.

UNITED STATES PATENT AND TRADEMARK OFFICE
CERTIFICATE OF CORRECTION

PATENT NO. : 5,090,993

DATED : February 25, 1992

INVENTOR(S) : Marcus P. Moon

It is certified that error appears in the above-identified patent and that said Letters Patent is hereby corrected as shown below:

Column 26, line 59, "1,3,5-triazin-2-yl]amino]carbonyl]amino]sulfonyl]-3-" should read --1,3,5-triazin-2-yl]amino]carbonyl]amino][sulfonyl]-3- --.

Column 26, line 63, "y)-1,3,5-triazin-2-yl]aminio]carbonyl]amino]-sul-" should read --y)-1,3,5-triazin-2-yl]aminio]carbonyl]amino][sul- --.

Signed and Sealed this

Twenty-ninth Day of November, 1994

Attest:

BRUCE LEHMAN

*Attesting Officer*   *Commissioner of Patents and Trademarks*